(12) United States Patent
Huang

(10) Patent No.: US 9,688,663 B2
(45) Date of Patent: Jun. 27, 2017

(54) CROSSLINKING REAGENTS, METHODS, AND COMPOSITIONS FOR STUDYING PROTEIN-PROTEIN INTERACTIONS

(71) Applicant: CellMosaic, Inc., Worcester, MA (US)

(72) Inventor: Yumei Huang, Lexington, MA (US)

(73) Assignee: Cell Mosaic, Inc., Woburn, MA (US)

( * ) Notice: Subject to any disclaimer, the term of this patent is extended or adjusted under 35 U.S.C. 154(b) by 0 days.

(21) Appl. No.: 14/965,699

(22) Filed: Dec. 10, 2015

(65) Prior Publication Data
US 2016/0159777 A1    Jun. 9, 2016

Related U.S. Application Data

(63) Continuation of application No. 13/579,198, filed as application No. PCT/US2011/026579 on Mar. 1, 2011, now abandoned.

(60) Provisional application No. 61/309,512, filed on Mar. 2, 2010.

(51) Int. Cl.
| C07D 229/02 | (2006.01) |
| C07D 403/12 | (2006.01) |
| C07K 4/00 | (2006.01) |
| C07K 5/068 | (2006.01) |

(52) U.S. Cl.
CPC ......... *C07D 403/12* (2013.01); *C07D 229/02* (2013.01); *C07K 4/00* (2013.01); *C07K 5/06086* (2013.01)

(58) Field of Classification Search
None
See application file for complete search history.

(56) References Cited

PUBLICATIONS

Wlassoff, Wjatschesslaw A. et a, "Synthesis and characterization of (d)ntp derivatives substituted with residues of different photoreagents." Bioconj. Chem. (1995) 6 p. 352-360.*
The ThermoFisher web page describing photoreactive crosslinker chemistry, https://www.thermofisher.com/us/en/home/life-science/protein-biology/protein-biology-learning-center/protein-biology-resource-library/pierce-protein-methods/photoreactive-crosslinker-chemistry.html, downloaded Oct. 28, 2016.*

* cited by examiner

*Primary Examiner* — Fred Reynolds
(74) *Attorney, Agent, or Firm* — Milstein Zhang & Wu LLC

(57) ABSTRACT

The invention provides reagents, methods, and compositions for studying protein-protein interactions. The inventive system and methods allow the analysis of protein-protein interactions in vivo and in vitro. Advantages offered by various embodiments of the inventive system and methods compared to existing photocrosslinking approaches include, for example, (i) novel reversible crosslinking reagents that allow easy isolation, purification, and enrichment of the crosslinked products; (ii) trifluoromethyl phenyldiazirine- or perfluorinaled phenylazide-based photocrosslinking reagents that provide high specific labeling, no side product, and higher photocrosslinking efficiency; (iii) versatile spacer groups that allow systematic contact site mapping; (iv) novel methods for isolating, purifying, and detecting crosslinked products based on the reversible-link chemistry; and (v) the ability to study the interaction sites in vitro, in situ, or in vivo.

2 Claims, 16 Drawing Sheets

Fig. 1 Reversible crosslinking agents I, II, III, and IV

FG2—SP1—W   (I)

FG2 is a functional group capable of forming a reversible linker, SP1 is a spacer group, W is a chemical- or photocrosslinking group.

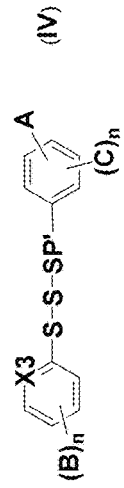

$R_1$, $R_2$ —N—X—SP1—W   (II)

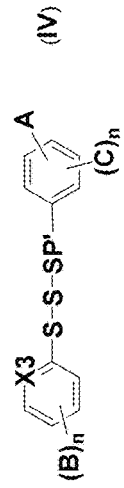

where X2 is O or S; R3 and R4 are an independent H, alkyl, or aromatic group; R1 and R2 are and independent H, alkyl, or aromatic group.

X is —O-, —NH- or

V—SP2—L—SP1—W   (III)

V is a chemical crosslinking group,
SP1 and SP2 are each independent spacer groups.
L is a reversible linker that can be formed and unformed or broken apart with particular chemical treatment.

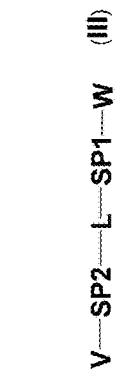

(IV)

X3 is N or C.
B and C independently represent H, a halogen, nitro, cyano, carbonyl, carboxyl, hydroxyl, amido, or amino group; an unsubstituted hydrocarbon group of less than 15 atoms; a hydrocarbon group of less than 15 atoms; or a hydrocarbon group of less than 15 atoms and substituted with at least one of the aforementioned groups.
n is an integer from 0 to 4.
A is an azide or trifluoromethyl diazirine group. When A is an azide group, C is fluorine when n is an integer from 1 to 4.
SP' is a spacer group.

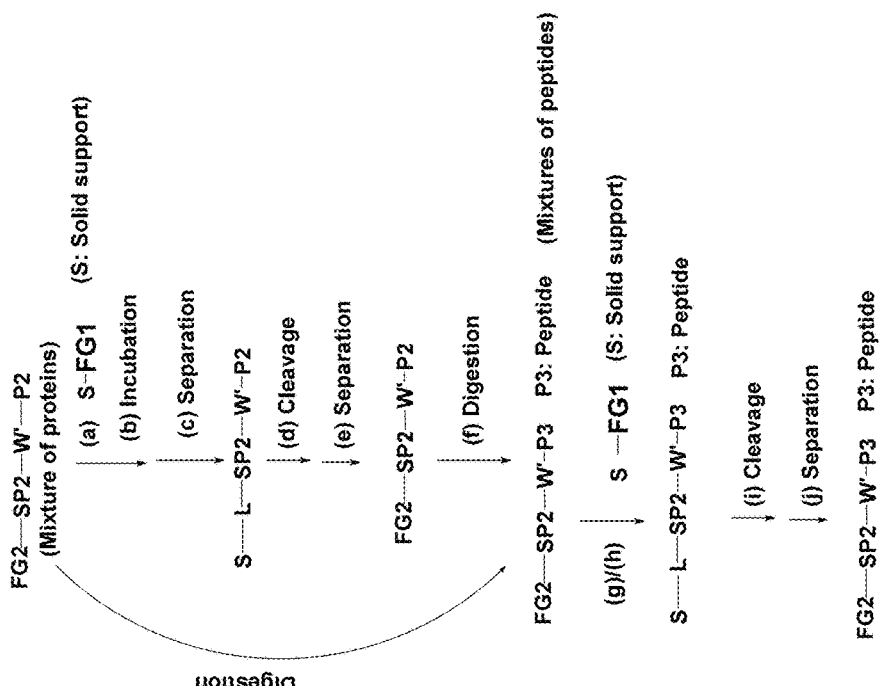
Fig. 2 Method for covalently capturing an interaction between two proteins
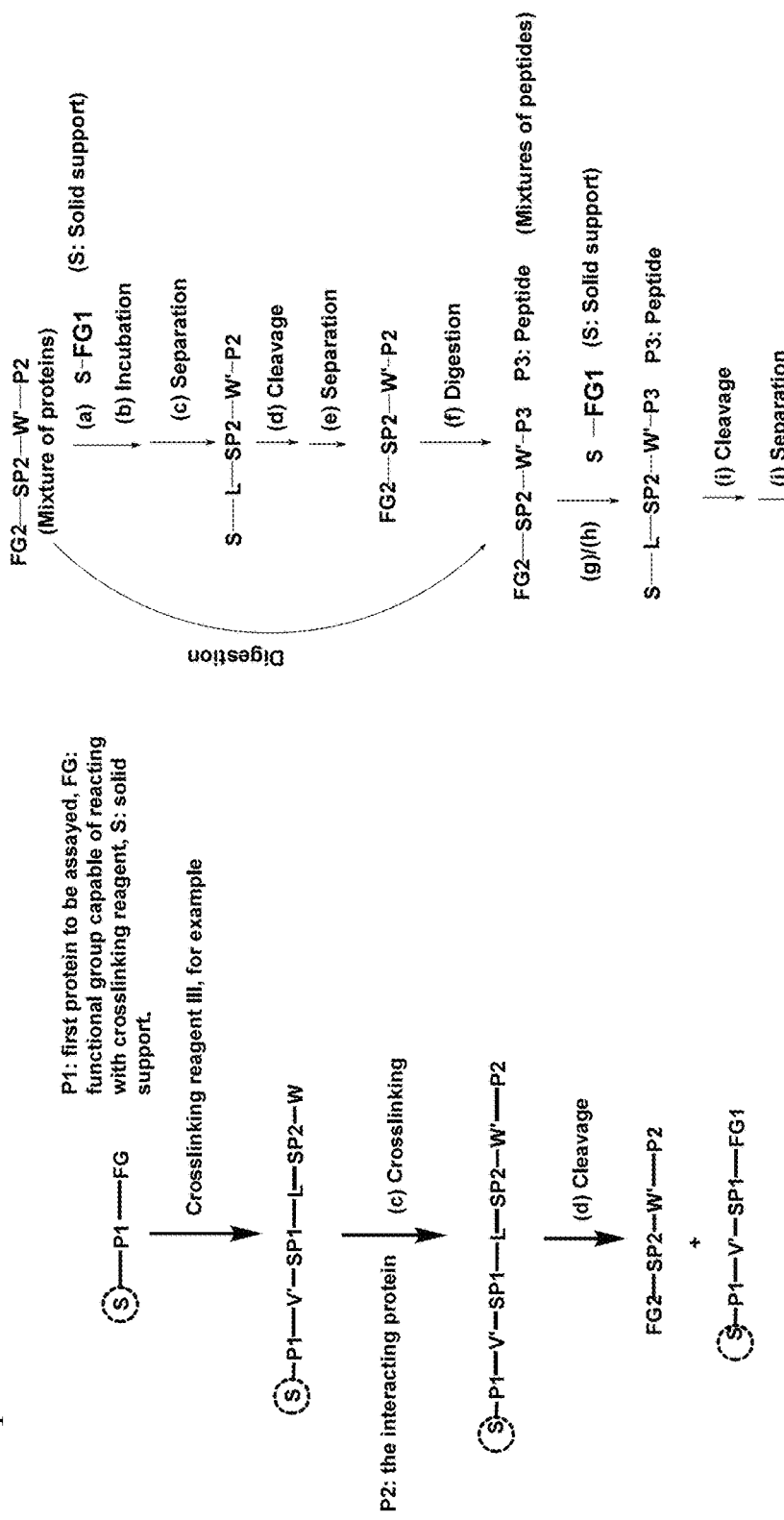
Fig. 3 Method for isolating crosslinked products

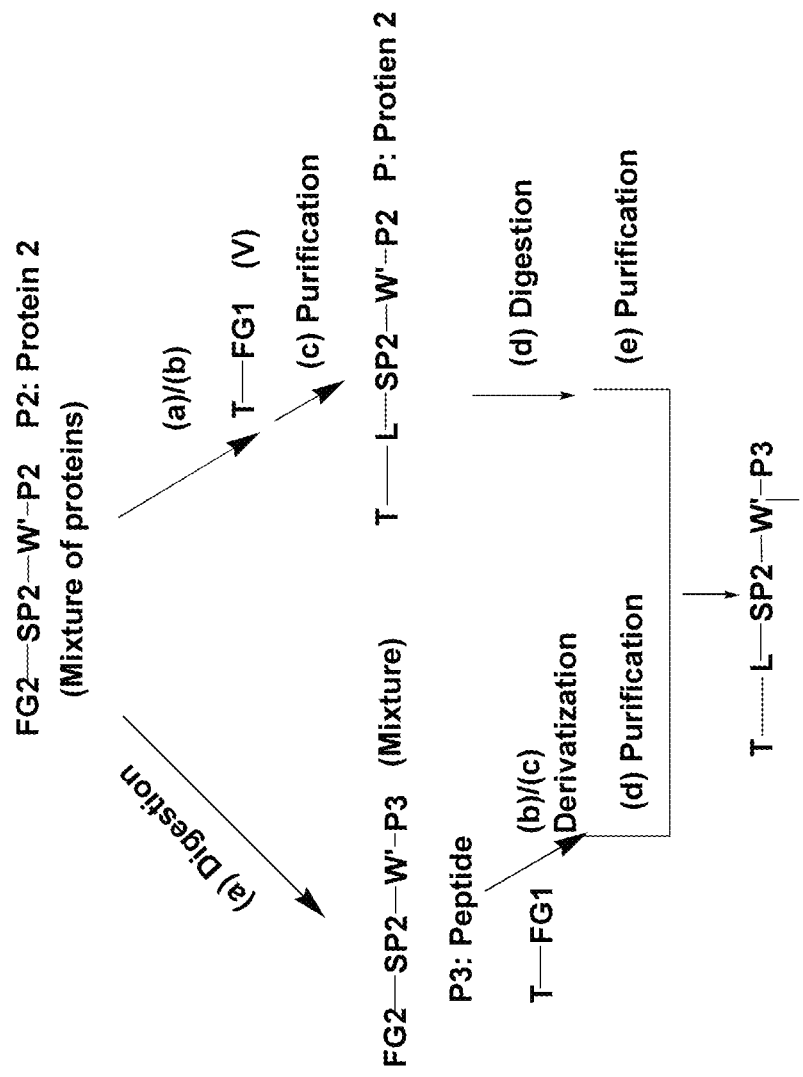
Fig. 4 Method for purifying crosslinked products

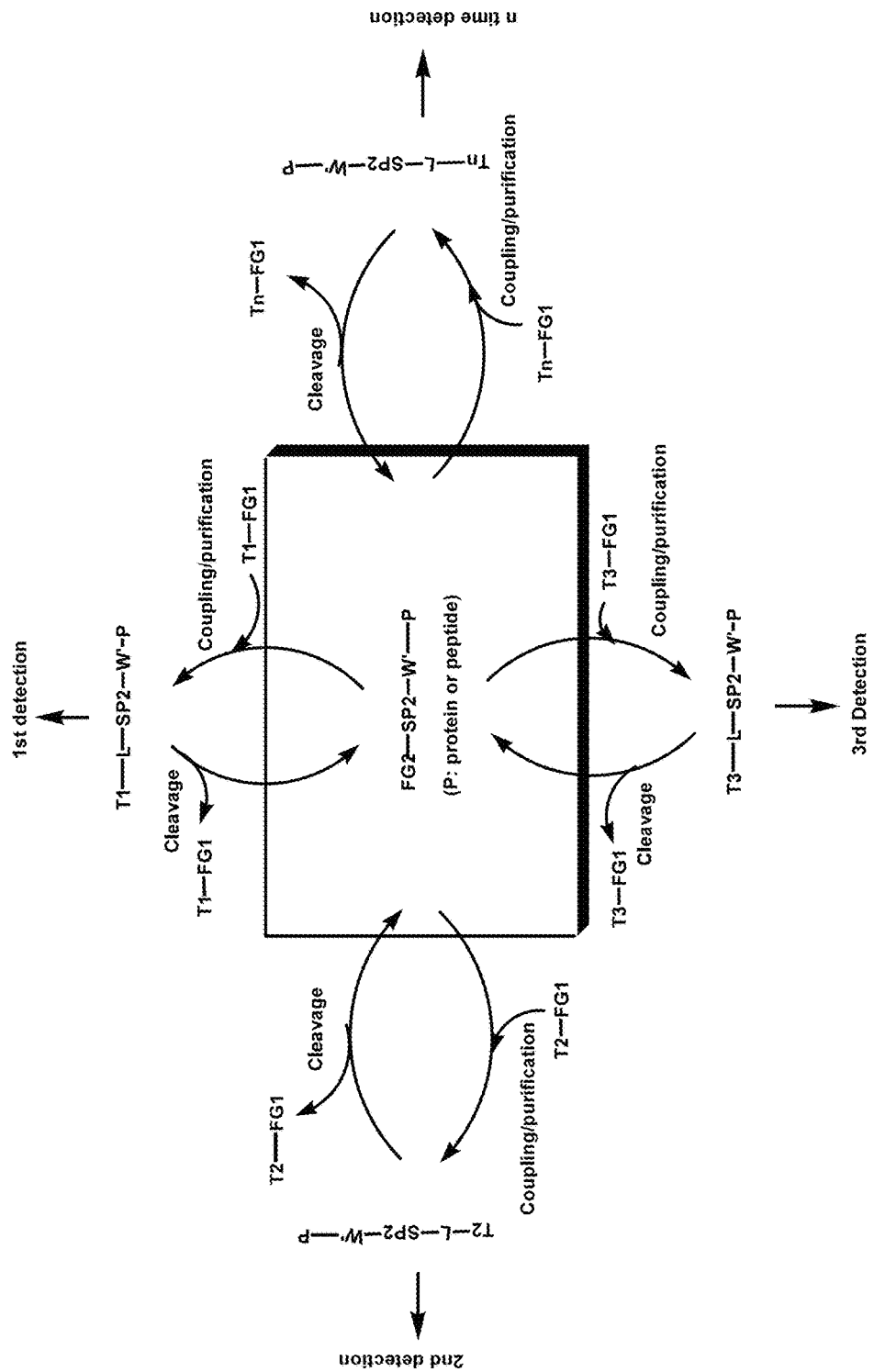
Fig. 5 Multi-dimensional detection method

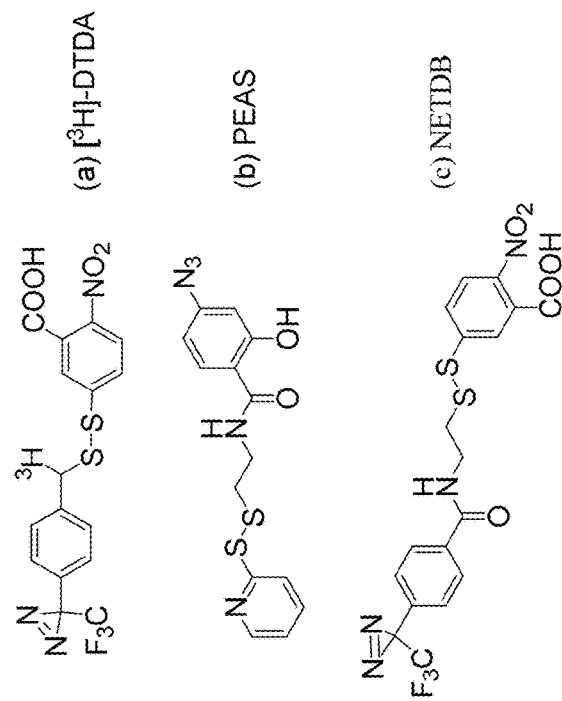
Fig. 7 Photocrosslinking reagents used in Khorana's lab to study protein–protein interactions
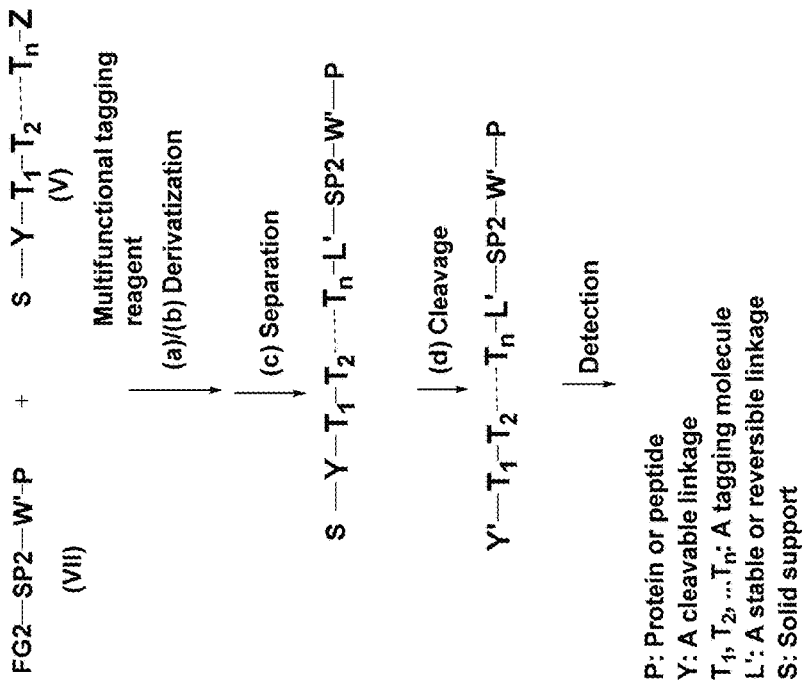
Fig. 6 Single multifunctional tag for multi-dimensional detection

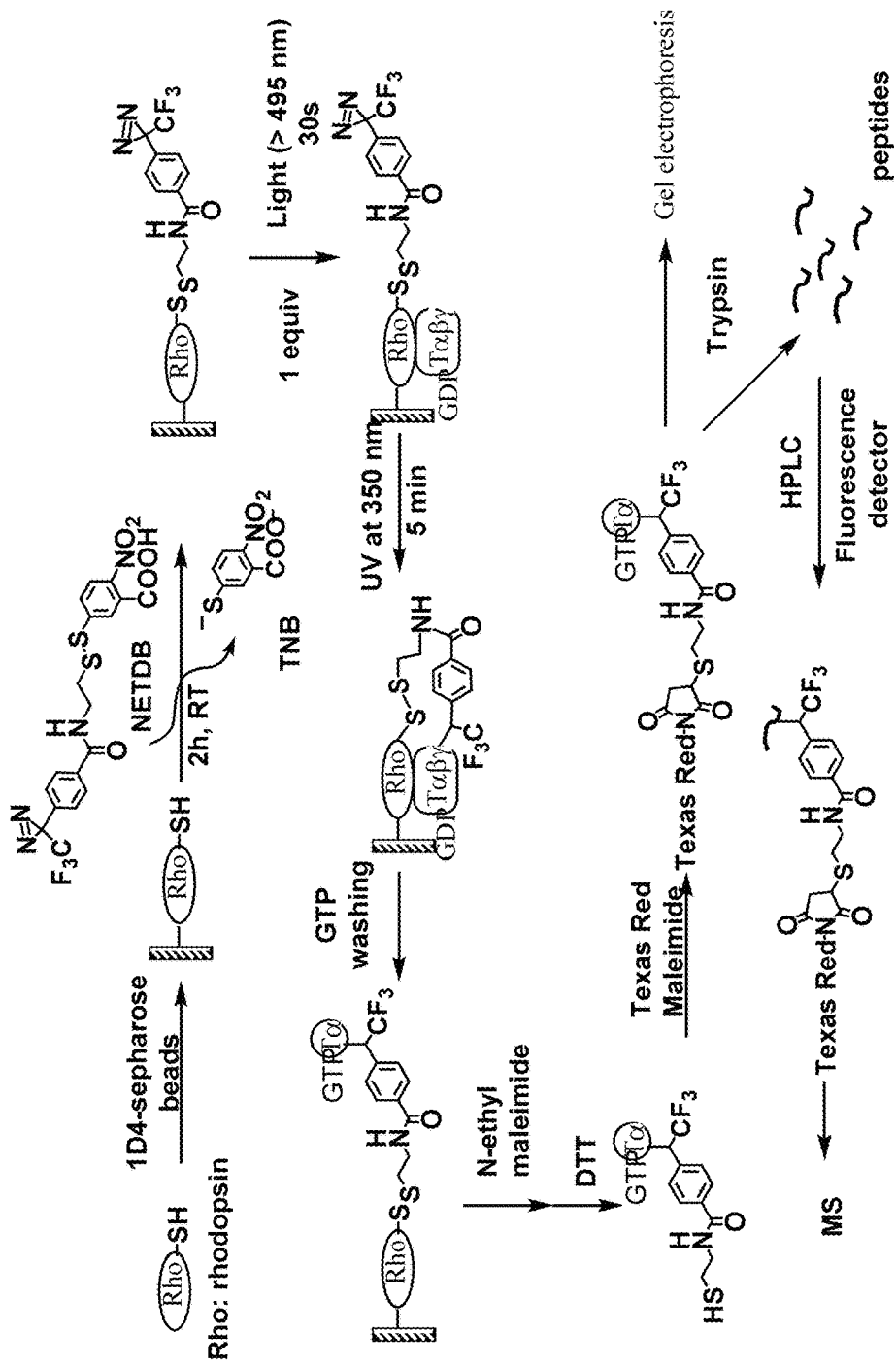
Fig. 8 Approaches for photocrosslinking rhodopsin with transducin

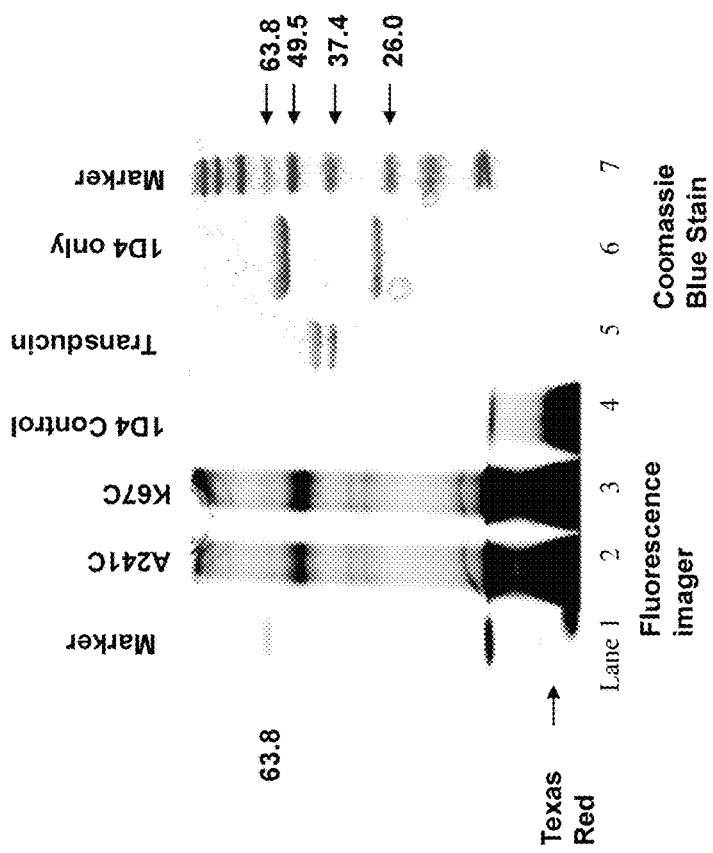
Fig. 9 SDS/PAGE of crosslinked product from rhodopsin A241C, K67C
• The control experiment was performed using 1D4-sepharose beads without rhodopsin.

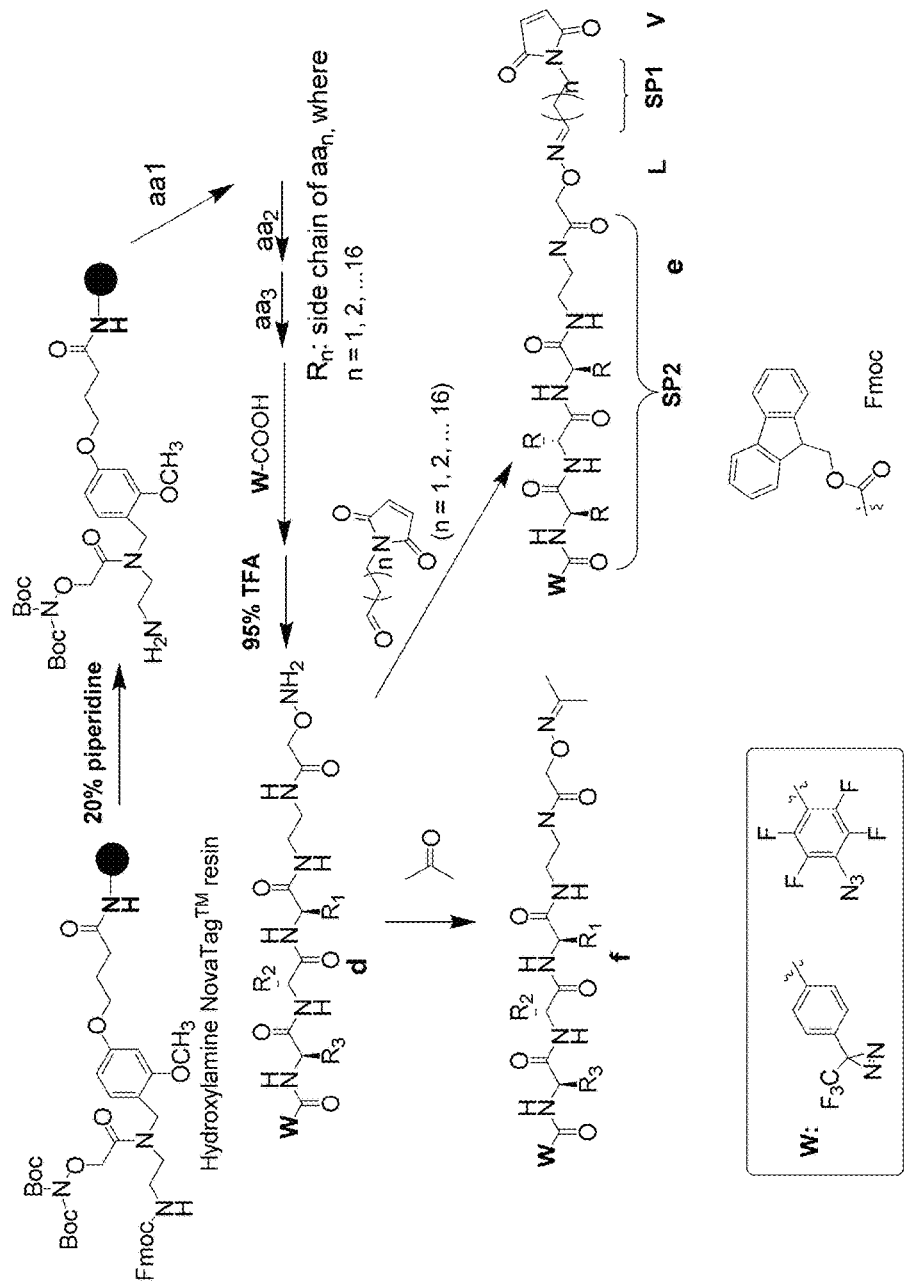
Fig. 10 Example 1

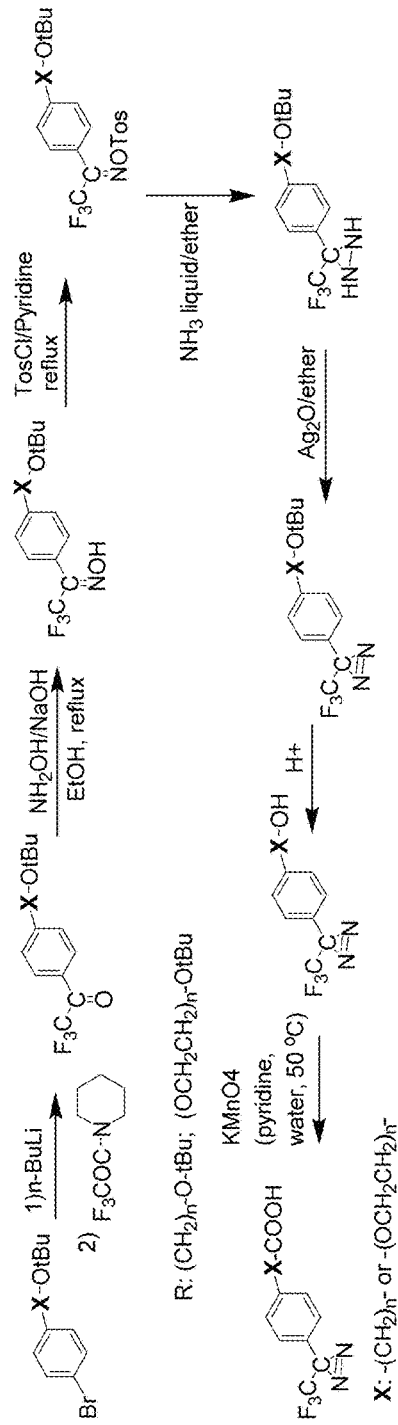
Fig. 11 Example 2
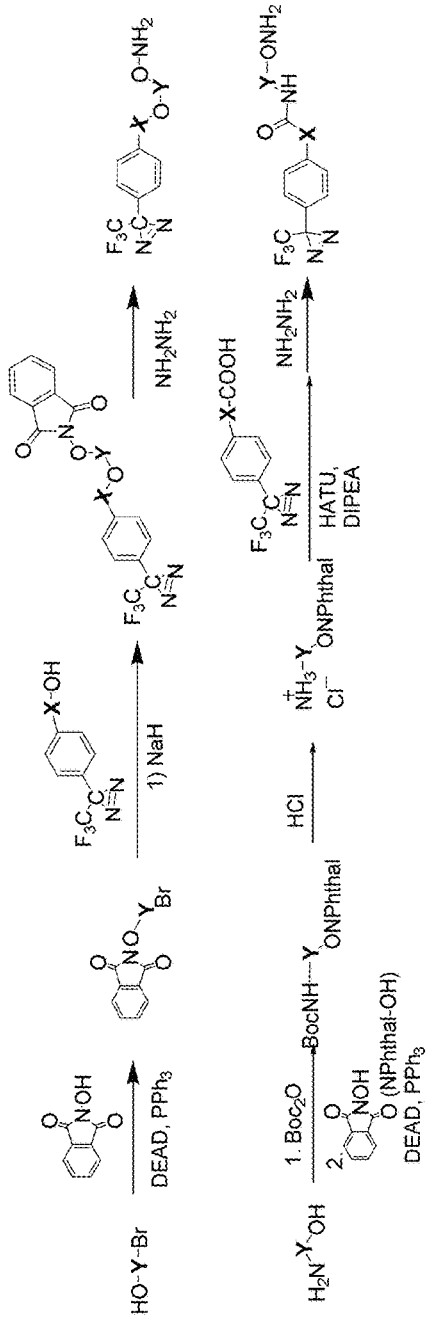
Fig. 12 Example 3

Fig. 13 Example 4
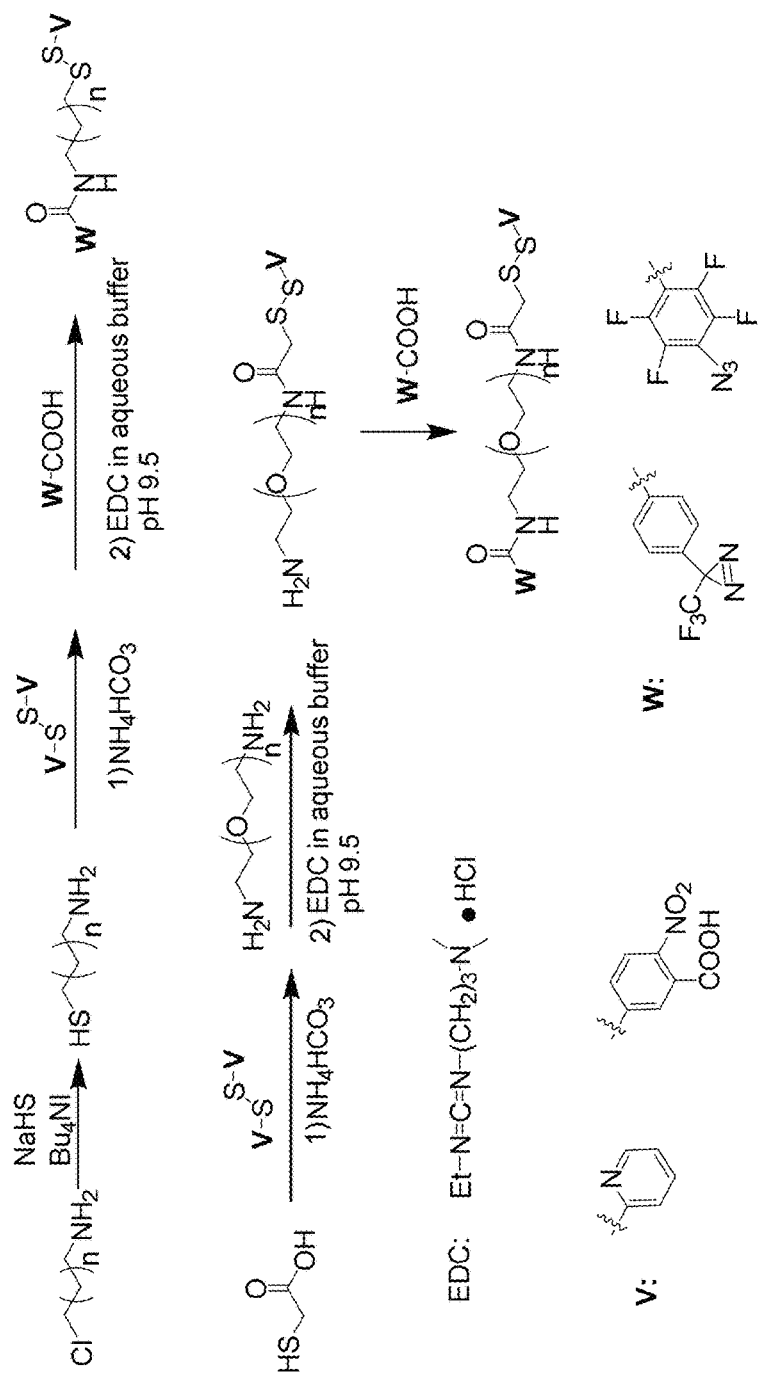

Fig. 14 Example 5
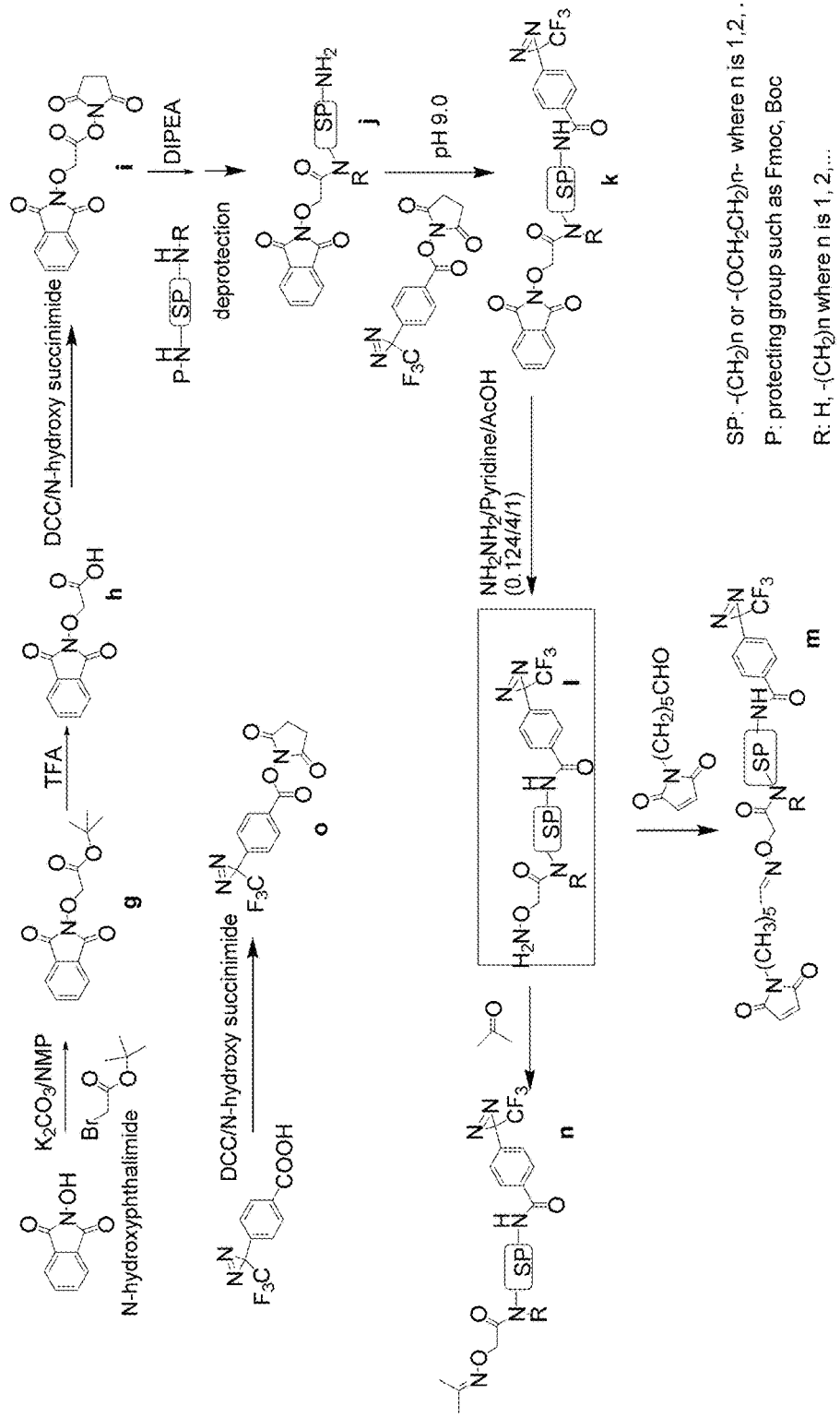

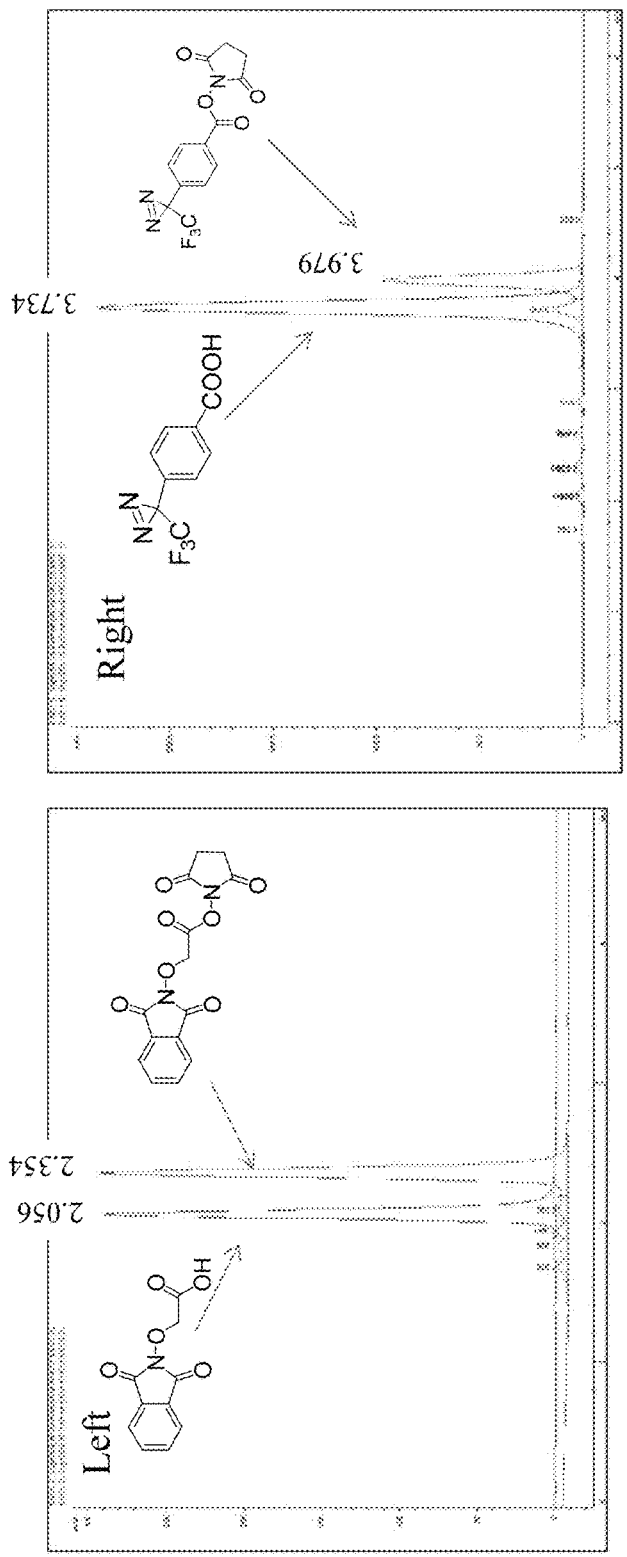
Fig. 15 HPLC analysis of the NHS ester formation for N-phthalimidooxyacetic acid (Left) and diazirine compound (Right)
HPLC conditions:
column: Xterra™ RP18, 5 um, 4.6 x250 mm
Buffer A: 0.1% TFA in water
Buffer B: 0.1% TFA in acetonitrile
Elute: isocratic 60% B

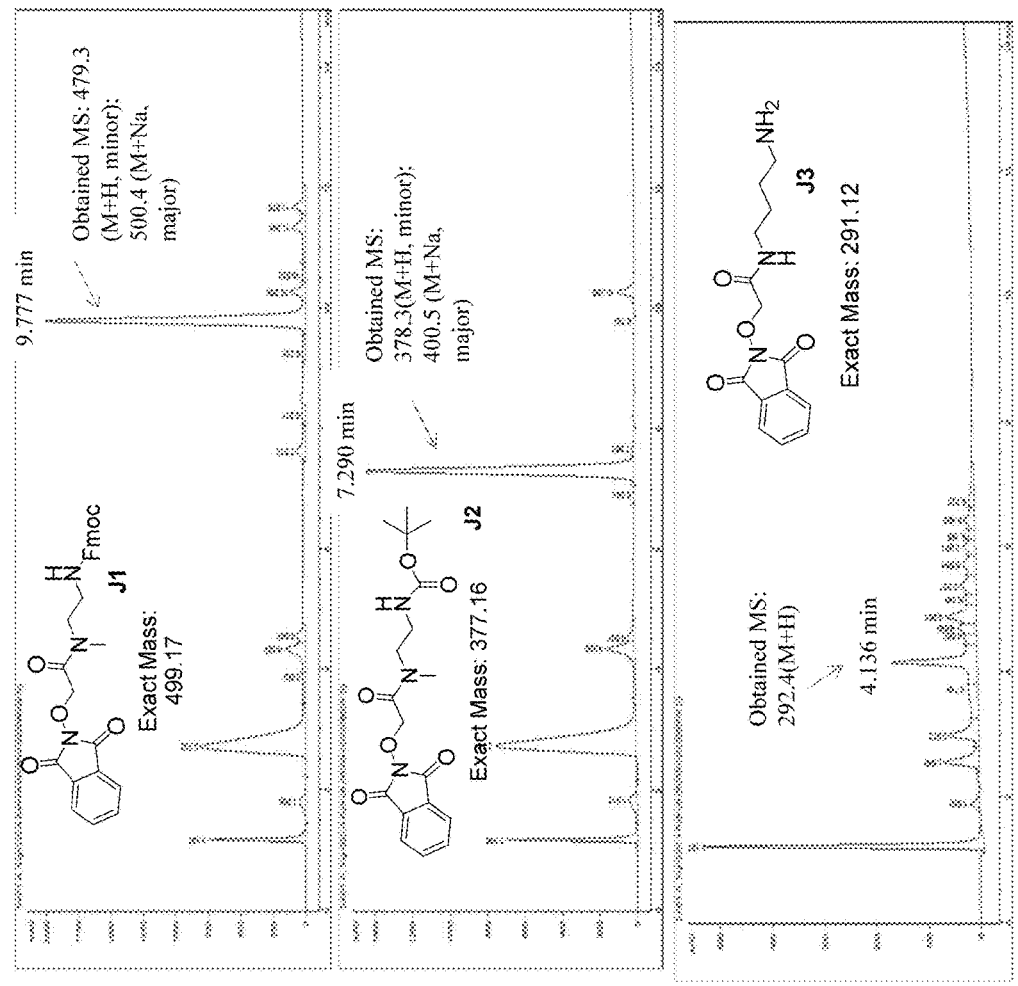

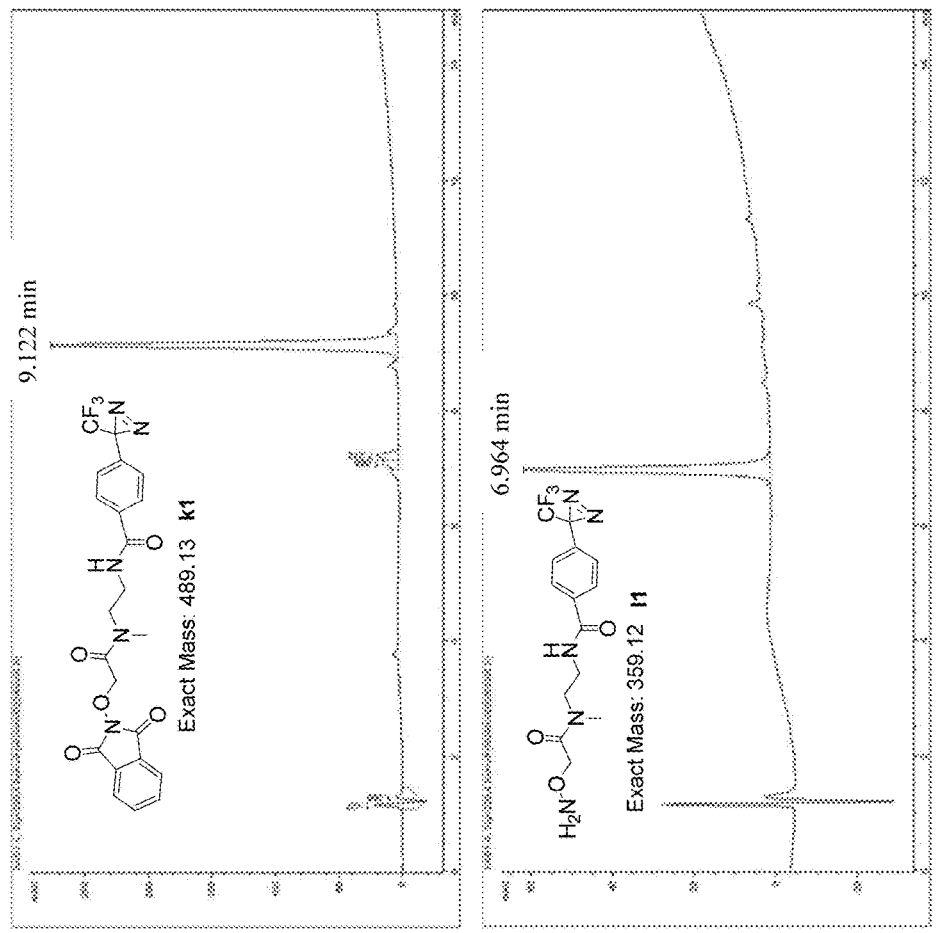
Fig. 17 HPLC analysis of compound k1 and l1

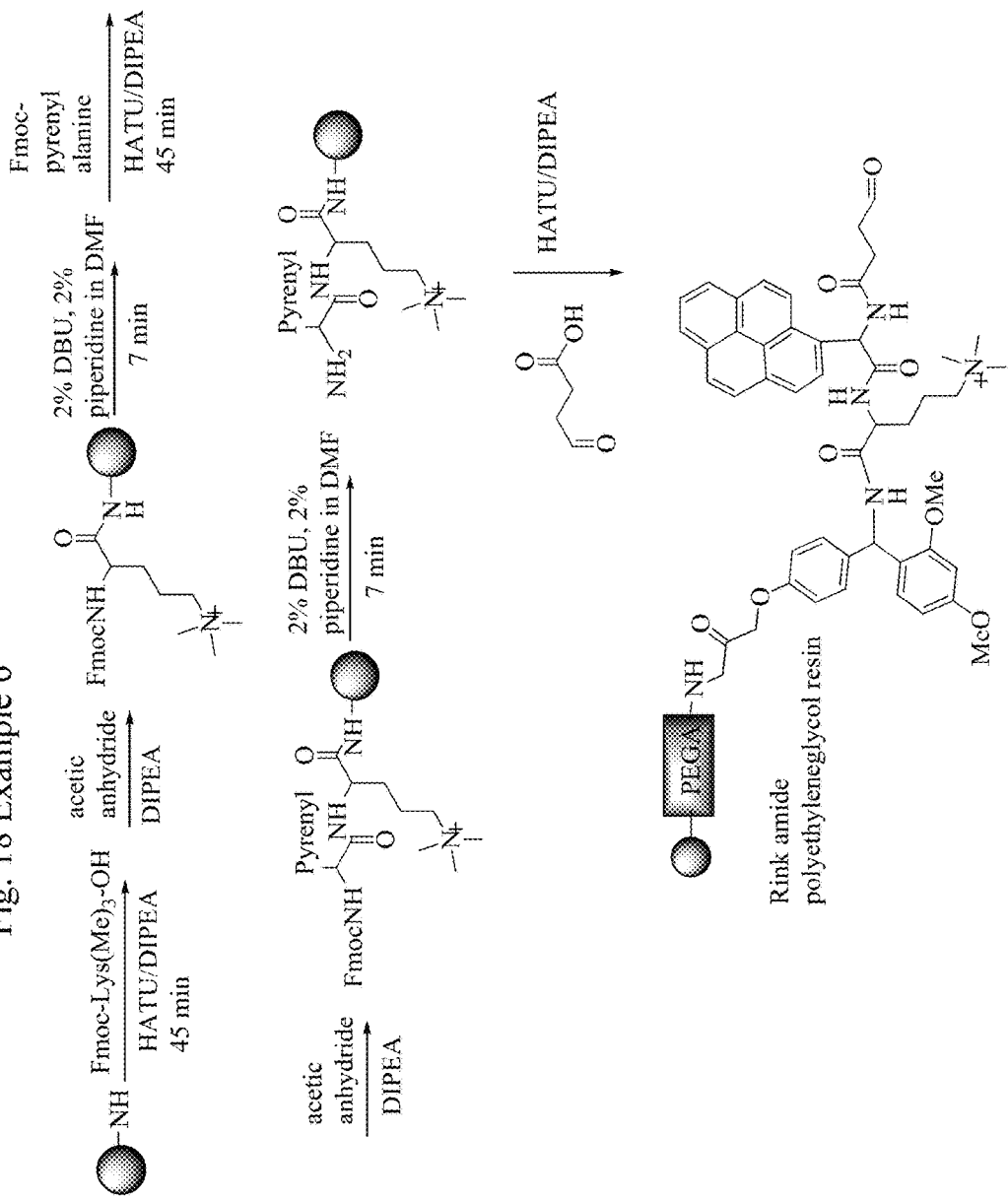
Fig. 18 Example 6

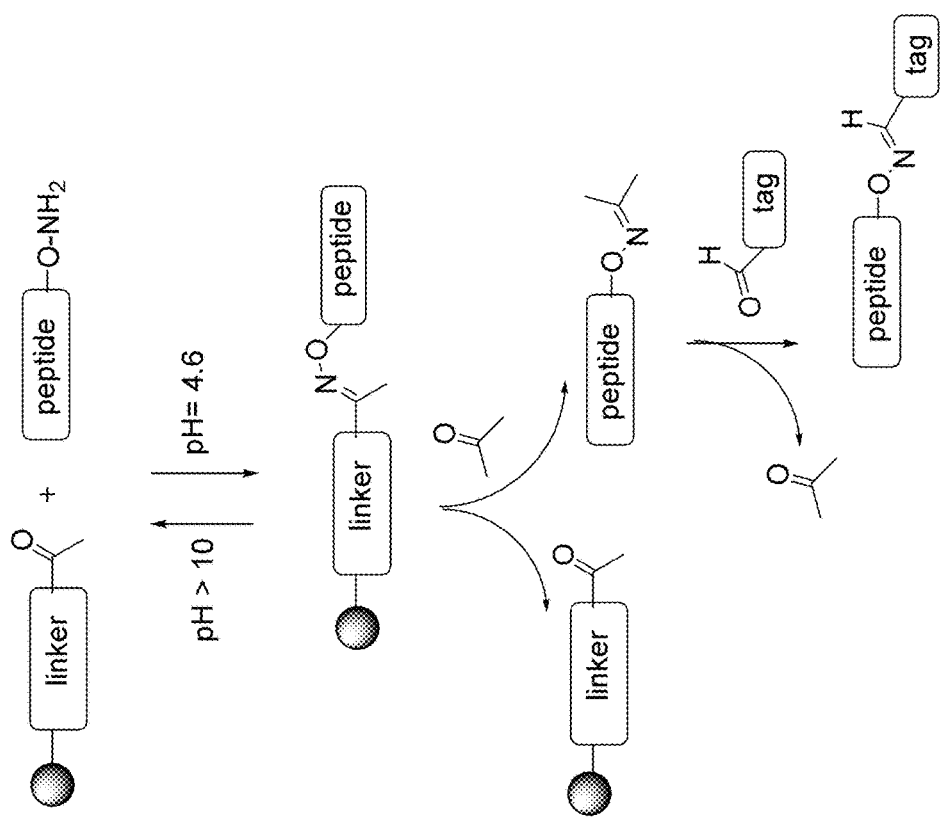
Fig. 19 Example 7

CROSSLINKING REAGENTS, METHODS, AND COMPOSITIONS FOR STUDYING PROTEIN-PROTEIN INTERACTIONS

PRIORITY CLAIMS

This application is a continuation of U.S. application Ser. No. 13/579,198, filed Aug. 15, 2012, which is the national stage of International (PCT) Patent Application No. PCT/US2011/026579, filed Mar. 1, 2013, and published under PCT Article 21(2) in English, which claims the benefit of priority from U.S. Provisional Application Ser. No. 61/309,512, filed Mar. 2, 2010, the entire content of each of which is incorporated herein by reference for all purposes.

FIELD OF THE INVENTION

The present invention relates to crosslinking reagents, methods and compositions useful for the investigation and manipulation of protein-protein interactions. More particularly, the invention relates to compositions and methods for identifying the binding subunits and mapping the contact sites of protein-protein interactions at the molecular level, and applications based thereon.

BACKGROUND

Protein-protein interactions play an important role in regulating the physiological functions in cells, such as gene expression, transport, signal transduction and cell cycle control. Identification of the interacting protein partners and the contact sites involved can facilitate the understanding of protein functionalities and assist in identifying and providing novel approaches for the development of treatment and diagnostic methods and agents. Due to the fact that many interactions between proteins are transient, however, the general techniques for elucidating the three-dimensional structure of the complexes, such as X-ray and NMR, are not particularly useful due to technical difficulties. Alternative biochemical approaches need to be developed for structure—function studies of protein-protein interactions.

Crosslinking reagents are promising tools for studying protein-protein interactions (e.g., Freedman, R. B. *Mends Biochem. Sci.* 1979, 193-197; Herrmann, et al. *Methods Cell Biol.* 2001, 65, 217-230; Fancy, D. A. *Curr. Opin. Chem. Biol.* 2000, 4, 28-32; Fasold, et al. *Angew. Chem. Internat. Edit.* 1971, 10, 795-801). Crosslinking reagents are, in general, small organic molecules containing two chemical groups (bifunctional) that react with the functional groups on the side chains of proteins. Proteins in proximity to one another can be connected covalently via crosslinking reagents. There are two types of crosslinking reagents. The first type is photoactivable crosslinkers, which can be incorporated by photolysis. The second type is chemical crosslinkers, which can be incorporated under particular chemical conditions. Covalent crosslinking using photoactivable reagents is a preferred method for studying transient protein-protein interactions due to their highly reactive and non-specific insertion properties with any proximal C—H bond.

Khorana's laboratory has been at the forefront of developing useful photocrosslinking strategies for studying the structure and function of protein-protein interactions at the molecular level, using rhodopsin as a model system over the last few decades. For example, the crosslinking reagent 3-(4-(((4-nitro-3-carboxyphenyl)dithio)methyl-t)-phenyl)-3-(trifluoromethyl)-3H-diazirine (DTDA, FIG. 7a; Resek, et al. *J. Org. Chem.* 1993, 58, 7598-7601) was designed with several specific features for studying rhodopsin-transducin interactions. DTDA is able to form a disulfide bond with accessible cysteines. In combination with site-specific rhodopsin mutants, DTDA can be targeted to unique positions in the protein. In addition, following the formation of carbene, the radioactive label can be transferred to the site of insertion after cleavage of the disulfide bond. This chemical has been applied successfully to the determination of the binding subunit of transducin (Resek, el. al. *Pro. Natl. Acad. Sci. USA*. 1994, 91, 7643-7647) using gel electrophoresis and fluorographic visualization. However, DTDA is not widely used due to the difficult synthetic procedures and the radioactivity.

In order to characterize the contact sites of the interacting proteins, this method has been developed further in Khorana's lab to include protcomic digestion, streptavidin/biotin purification of peptide fragments and mass spectrometry. A commercially available nitrene-generating arylazide, N-((2-pyridyldithio)ethyl)-4-azido salicylamide (PEAS, FIG. 7b) was used (Cai, et. al. *Proc. Natl. Acad. Sci. USA*. 2001. 98, 4877-4882). This method has several drawbacks. i) The data is uncertain and crosslinking is inefficient due to the use of an inferior photocrosslinking reagent. Photolysis of simple arylazide releases singlet nitrene, which can isomerize rapidly (10-100 ps) to strongly electrophilic species (benzazirine and cycloheptatetraenes) and undergo bimolecular reactions at room temperature (Gritsan et al. *J. Am. Chem. Soc.* 2001, 123, 1951-1962). This reaction results in the crosslinking of amino acids that are not in the vicinity of contact sites. Simple arylnitrene also cannot insert into non-activated C—H bonds and results in a very low yield of crosslinking products. ii) Current methods do not provide a means for the efficient capture and elution of crosslinked products for mass spectrometric analysis. Photocrosslinking generally produces heterogeneous crosslinked products at low concentrations: Presently, the most commonly used purification handle for crosslinked products is the sulfhydryl functional group, through which biotin is introduced. This biotin molecule allows the non-covalent capture of crosslinked products through immobilized avidin, and the crosslinked products are eluted out with a large excess of biotin. In such non-covalent capture systems, however, the trapped crosslinked products may be diluted or lost during the washing steps. The presence of a large excess of biotin suppresses the mass sensitivity. iii) A third drawback is due to issues associated with sulfhydryl compounds. Thiol chemistry is not orthogonal to peptide chemistry. Any Cys residues on a protein have to be blocked before the introduction of a biotin moiety. Blocking adds an extra step and complicates data analysis. Also, when working with a very dilute solution (e.g., in the femtomole range), tryptic fragments originating from any contaminates, such as cytokeratin (from the hair), that carry a Cys may react with biotin and interfere with the mass spectrum data. Finally, to prevent the oxidation of free thiol, a reducing/inert environment must be maintained throughout the process. Ideally the purification handle should be orthogonal to peptide functional groups.

This general methods have been further improved in Khorana's lab by Y. Huang using a newly synthesized DTDA analog compound, N-(2-(4-nitro-3-carboxyphenyl)dithioethyl)-4-(3-(trifluoromethyl)-3H-diazirine-3-yl)-benzamide (NETDB, FIG. 7c) and a fluorescence tag purification strategy (FIG. 8). HPLC is used to purify crosslinked peptides digested by trypsin (Huang, Y., Khorana, H. G. "Mapping of Contact Sites in Interaction between Transducin and Light-Activated Rhodopsin." 17th Symposium of the Protein Society, Jul, 26-30, 2003, Boston, Mass.). The photocrosslinking yield is increased substantially and the crosslinked subunit can be easily detected by fluorescence imager (FIG. 9). Some tryptic peptides have been identified. However, no contact sites have yet been identified on the molecular level.

A few issues remain to be solved if a general approach is established for structural determination of interacting proteins at the molecular level: i) new and efficient crosslinking reagents for capturing the interacting proteins; ii) crosslinking reagents with a variable spacer for determining the distance between the contact sites; iii) method for separation, purification, and sample enrichment to enhance detection, for example, by mass spectrometric analysis; iv) multiple detection methodologies; v) a method for detecting protein-protein interactions in a system that does not require proteins to be purified; and vi) the replacement of cleavable disulfide linkages.

SUMMARY OF THE INVENTION

The present invention is based, in part, on the discovery of methods and crosslinking reagents that are useful for identifying and quantifying the protein partners involved in interactions and/or for characterizing the contact sites of protein-protein interactions at the molecular level. The system and methods of the invention allow the analysis and characterization of the interactive protein partners in a system where the protein does not have to be purified, such as in a membrane or cellular system. Furthermore, the system and methods of the invention allow the mapping of the contact sites for the protein-protein interactions at the molecular level. Advantages offered by various embodiments of the invention compared to existing photocrosslinking approaches include, for example: (i) new reversible crosslinking reagents that allow easy isolation, purification, and enrichment of the crosslinked products; (ii) trifluoromethyl phenyldiazirine- or perfluororated phenylazide-based photocrosslinking reagents that result in highly specific labeling, no side products, and higher photocrosslinking efficiency; (iii) inclusion of modular spacer groups in the crosslinking reagent that allow systematic mapping of the contact sites; (iv) methods for the isolation, purification, and detection of crosslinked products based on oxime, hydrazone, semicarbazone, or thiosemicarbazone linkages; and (iv) the ability to study the interaction sites in vitro, in situ, or in vivo.

The present invention provides methods, compositions and kits for assaying protein-protein interactions and/or characterizes known and novel protein-protein interactions. For example, the present invention provides a method of assaying protein-protein interactions in a collection of cells where individual cells express the protein of interest that incorporates an amino acid, such as Cys, or an aldehyde amino acid analog at a specific position that allows the introduction of crosslinking reagent in vivo. Therefore, the present invention may be used to identify those proteins that interact with the protein of interest and the amino acids that are in contact with the proteins. By varying the position of the amino acids and/or using systematically designed crosslinking reagents, the method allows the mapping of the contact sites between two proteins.

Additionally, the present invention may be used to characterize known and novel protein-protein interactions under a variety of chemical, genetic, nutritional and environmental conditions. For example, the effects of molecules or chemicals that enhance or disrupt protein-protein interactions at the molecular level may be assayed. Also, protein-protein interactions may be assayed in cell lines bearing different genetic backgrounds, such as the presence or absence of oncogenes.

Additionally, the present invention may be used to characterize known protein-protein interactions in vitro using purified protein or part of tissues and cells containing the protein of interest. For example, the protein may be genetically modified to contain a single functional group for incorporating crosslinking reagent.

In one aspect, the invention generally relates to a crosslinking reagent having the Formula (I)

FG2-SP1-W      (I)

wherein
FG2 is a chemical functional group selected from the group consisting of an aminooxy group, an aldehyde group, a keto group, a hydrazide group, a semicarbazide group, and a thiosemicarbazide group;
SP1 is a spacer group selected from the group consisting of a bond, a substituted or unsubstituted ($C_1$-$C_{24}$) alkyl group, a substituted or unsubstituted ($C_1$-$C_{24}$) heteroalkyl group, a polyethyleneglycol group, a polyalcohol group, a polyamine group, a polyester group, a polyphosphodiester group, a peptide, and a peptidomimetics group; and
W is a chemical- or photocrosslinking group selected from the group consisting of an aryl ketone group, an azide group, a diazo group, a diazirene group, a ketene group, an olefin group, a dicarbonyl group, an epoxide group, an organosilane group, an isothiocyanate group, an isocyanate group, an acyl azide group, an ester group, a sulfonyl chloride group, a carbonate group, an imidoester group, an anhydride group, a haloacetyl group, an alkyl halide group, a maleimide group, a vinylsulfone group, a thioester group, a disulfide group, and a sulfhydryl group, In some embodiments, the ester group is selected from N-hydroxylsuccinimide esters and fluorophenyl ester groups. W may be a substituted or unsubstituted trifluoromethyl phenyl diazirine group. In certain embodiments, W is a perfluorinated phenyl azide group. In certain other embodiments, W is a haloacetyl group, an alkyl halide group, a maleimide group, or an N-hydroxylsuccinimide ester group.

In another aspect, the invention generally relates to a crosslinking reagent having the Formula (II)

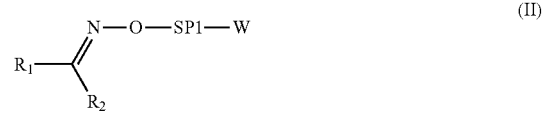

wherein
$R_1$ and $R_2$ are independently a H, a $CH_3$, a substituted $C_1$-$C_5$ alkyl group, or an aryl group;
SP1 is a spacer group selected from the group consisting of a bond, a substituted or unsubstituted ($C_1$-$C_{24}$) alkyl group, a substituted or unsubstituted ($C_1$-$C_{24}$) heteroalkyl group, a polyethyleneglycol group, a polyalcohol group, a polyamine group, a polyester group, a polyphosphodiester group, a peptide, and a peptidomimetic group; and
W is a chemical or photo crosslinking group selected from the group consisting of an aryl ketone group, an azide group, a diazo group, a diazirene group, a ketane group, an olefin group, a dicarbonyl group, an epoxide group, an organosilane group, an isothiocyanate group, an isocyanate group, an acyl azide group, an N-hydroxylsuccinimide ester group, a fluorophenyl ester group, a sulfonyl chloride group, a carbonate group, an imidoester group, an anhydride group, a haloacetyl group, an alkyl halide group, a maleimide group, a vinylsulfone group, a thioester group, a disulfide group, and a sulfhydryl group.

In yet another aspect, the invention generally relates to a crosslinking reagent having the formula (III)

$$V—SP2-L-SP1-W \quad (III)$$

wherein

V is a chemical crosslinking group selected from the group consisting of an isothiocyanate group, an isocyanate group, an acyl azide group, an ester group, a sulfonyl chloride group, a carbonate group, an imidoester group, an anhydride group, a haloacetyl group, an alkyl halide group, a maleimide group, a vinylsulfone group, and a thioester group;

W is a chemical- or photo-crosslinking group selected from the group consisting of an aryl ketone group, an azide group, a diazo group, a diazirene group, a ketene group, an olefin group, a dicarbonyl group, an epoxide group, an organosilane group, an isothiocyanate group, an isocyanate group, an acyl azide group, an ester group, a sulfonyl chloride group, a carbonate group, an imidoester group, an anhydride group, a haloacetyl group, an alkyl halide group, a maleimide group, a vinylsulfone group, a thioester group, a disulfide group, and a sulfhydryl group;

each of SP1 and SP2 is independently a spacer group selected from the group consisting of a bond, a substituted or unsubstituted ($C_1$-$C_{24}$) alkyl group, a substituted or unsubstituted (C1-C24) heteroalkyl group, a polyethyleneglycol group, a polyalcohol group, a polyamine group, a polyester group, a polyphosphodiester group, a peptide, and a peptidomimetics group; and L is an oxime bond.

In yet another aspect, the invention generally relates to a reagent for protein or peptide labeling having the formula (V):

$$S—Y-T_1-T_2 \ldots T_n-Z \quad (V)$$

wherein

S is a solid support;

Y is a cleavable linkage;

$T_1, T_2, \ldots T_n$ is a tagging molecule;

n is an integer selected from 1, 2, 3, 4, 5, and 6; and

Z is a crosslinking group capable of reacting with an aldehyde, a keto, or an aminooxy.

In yet another aspect, the invention generally relates to a method for characterizing an interaction between two proteins. The method includes:

providing a first protein to be assayed, wherein the first protein is in a cellular environment, in a mixture of proteins, in a membrane, or purified and comprises a functional group selected from sulfhydryl group, aldehyde, keto, aminoxyl, hydrazide, or amine;

providing a reversible crosslinking reagent that having formula (I), (II), or (III);

combining the first protein and the reversible crosslinking reagent under conditions that permit the incorporation of the crosslinking group into the first protein;

providing an interacting protein partner and combining the interacting protein partner with the first protein under conditions where the first protein interacts with the second protein, thereby bringing it into reactive proximity of the crosslinking group and the second protein when photolysis or chemical conditions are applied to form a covalently stabilized protein complex; and incubating the crosslinked protein complex under cleavage conditions that break off the reversible linkage and release the first protein and the crosslinked interacting protein partner bearing a functional group.

In some embodiments, the first protein is a membrane protein or a G-protein coupled receptor. In certain embodiments, the first protein is attached to a solid support through non-covalent interaction or covalent crosslinking. In some embodiments, the support matrix comprises dextran, agarose, silica, synthetic polymer, or dextran, agarose, silica, or synthetic polymer covalently coupled to an antibody, ligand, or epitope tag. The interacting protein partner may be a membrane-associated protein or a G protein, for example.

In yet another aspect, the invention generally relates to a method for isolating a crosslinked product. The method includes:

providing a solid support bearing a first functional group capable of reacting with a second functional group to form a reversible linkage;

providing a mixture of non-crosslinked proteins and crosslinked protein bearing the second functional group;

combining the mixture of non-crosslinked and crosslinked proteins with a solid support under conditions that allow the formation of a reversible linkage through the reaction of the first functional group and the second functional group;

isolating the solid supported crosslinked second protein from non-crosslinked proteins;

incubating the solid supported second protein under conditions that allow release of the solid support bearing the first functional group thereby regenerating the crosslinked second protein bearing the second functional group;

isolating the crosslinked protein bearing the second functional group from the solid support;

digesting the crosslinked second protein to obtain a mixture of peptides, wherein the digestion is chemically, enzymatically, or both;

providing another solid support bearing the first functional group and mixing it with digested peptides under conditions that allow the formation of a reversible linkage through the reaction of the first functional group and the second functional group;

isolating the solid supported crosslinked peptides bearing the second functional group from non-crosslinked peptides;

incubating the solid supported crosslinked peptides in a minimum amount of cleavage buffer to regenerate the crosslinked peptides bearing the second functional group; and isolating the crosslinked peptides from the solid support and subjecting the peptides directly to detection.

In yet another aspect, the invention generally relates to a method for purifying crosslinked products. The method includes:

providing (i) a tagging molecule bearing a second functional group, wherein the second functional group is capable of reacting with the first functional group to form a reversible linkage, and (ii) a mixture of non-crosslinked proteins and the second crosslinked protein bearing the first functional group;

combing the mixture of non-crosslinked and crosslinked proteins with a tagging molecule under conditions that allow the formation of a reversible linkage through the reaction of the first functional group and the second functional group;

purifing the tagged second crosslinked protein from non-crosslinked proteins;

digesting the second crosslinked protein to obtain a mixture of peptides;

purifing the tagged crosslinked peptides from non-crosslinked peptides; and collecting and concentrating the crosslinked peptides for detection.

In yet another aspect, the invention generally relates to a method of detecting crosslinked protein or peptide. The method includes:

(a) providing tagging molecules with a first functional group and a protein or peptide containing a second functional group, wherein the second functional group is capable of reacting with the first functional group to form a reversible linkage;

(b) mixing protein or peptide with the first tagging molecule under conditions to form a reversible linker;

(c) subjecting the tagged protein or peptide to detection and/or purification method that is based on the first tagging molecule;

(d) cleaving the reversible linker to release the protein and peptide containing the second functional group;

(e) mixing protein with the second tagging molecules under conditions to form a reversible linker;

(f) subjecting the tagged protein or peptide to detection and/or purification method that is based on the second tagging molecule; and (g) repeating steps (c), (d) and (e) to allow the incorporation of other detection methods.

In some embodiments, the tagging molecule has formula (VI):

T-FG1     (VI)

wherein FG1 is a chemical functional group selected from the group consisting of aminooxy, aldehyde, keto, hydrazide, semicarbazide, and thiosemicarbazide; and T is a tagging moiety.

The protein or peptide may be detected using a technique selected from the group consisting of immunoassays, microarrays, microscopy, fluorescent microscopy, electron microscopy, electrophoresis, spectroscopy chromogenic reactions, radio-detection, enzymatic activity, photography, magnetic field measurements, sensors, electromagnetic energy detection, and chemical detection.

The spectroscopy may be SELDI, MALDI, electrospray mass spectroscopy, fluorescence spectroscopy, NMR , UV-Vis, or X-ray crystallography.

In yet another aspect, the invention generally relates to a covalent crosslinked protein or peptide having formula (VII):

FG2-SP2-W'-P     (VII)

wherein P is a protein or peptide;

SP2 is a spacer group selected from the group consisting of a bond, a substituted or unsubstituted ($C_1$-$C_{24}$) alkyl group, a substituted or unsubstituted ($C_1$-$C_{24}$) heteroalkyl group, a polyethyleneglycol group, a polyalcohol group, a polyamine group, a polyester group, a polyphosphodiester group, a peptide, a peptidomimetic group;

FG2 is a chemical functional group selected from the group consisting of aminooxy, aldehyde, keto, hydrazide, semicarbazide, and thiosemicarbazide; and W' is a connecting moiety formed by reacting W with functional groups in a protein or peptide, wherein W is a chemical- or photocrosslinking group selected from the group consisting of aryl ketones, azides, diazo compounds, diazirenes, ketenes, olefins, dicarbonyl groups, epoxides, organosilanes, isothiocyanates, isocyanates, acyl azides, active esters for example, carbonates, imidoesters, anhydrides, haloacetyl and alkyl halide derivatives, malcimides, vinylsulfone derivatives, thioesters, disulfides, and sulfhydryl group.

In yet, another aspect, the invention generally relates to a protein or peptide conjugate comprising a protein or peptide and a reversible crosslinking reagent. The conjugate has the following formula (VIII):

S'-L-SP2-W'-P     (VIII)

wherein

S' is a solid support or a detecting molecule;

P is a peptide or protein;

SP2 is a spacer group selected from the group consisting of a bond, a substituted or unsubstituted ($C_1$-$C_{24}$) alkyl group, a substituted or unsubstituted ($C_1$-$C_{24}$) heteroalkyl group, a polyethyleneglycol group, a polyalcohol group, a polyamine group, a polyester group, a polyphosphodiester group, a peptide, a peptidomimetic group;

L is a reversible linkage comprising an oxime, hydrazone, semicarbazone, or thiosemicarbazone bond;

W' is a connecting moiety formed by reacting W with functional groups in a protein or peptide, wherein W is a chemical- or photocrosslinking group selected from the group consisting of aryl ketones, azides, diazo compounds, diazirenes, ketenes, olefins, dicarbonyl groups, epoxides, organosilanes, isothiocyanates, isocyanates, acyl azides, active esters for example, but not limited to N-hydroxylsuccinimide esters and fluorophenyl esters, sulfonyl chlorides, carbonates, imidoesters, anhydrides, haloacetyl and alkyl halide derivatives, maleimides, vinylsulfone derivatives, thioesters, disulfides, and sulfhydryl group.

In some embodiments, S' is a solid support selected from a substituted or unsubstituted dextran, agarose, silica gel, or polyethylene glycol-linked solid support. In some other embodiments, S' is a moiety selected from the group consisting of fluorescent, radioactive, UV-active, isotopic, piperizine, tertiary amine, chromophore.The foregoing aspects and embodiments of the invention may be more fully understood by reference to the following figures, detailed description, and claims.

DEFINITIONS

The term "peptide", as used herein, refers to a polymer of amino acid residues linked together by a peptide bond. Typically, a peptide is at least two amino acids long. A peptide bond is commonly known in biochemistry as an amide linkage between the carboxyl group of one amino acid and the amino group of another. The preferred size of peptides ranges from 2 to 40 amino acids. The term peptide may also refer to amino acid polymers in which one or more amino acid residues is an artificial chemical analogue of a corresponding naturally occurring amino acid. An amino acid polymer in which one or more amino acid residues is an "unnatural" amino acid not corresponding to any naturally occurring amino acid is also encompassed by the use of the term "peptide" herein.

The term "protein", as used herein, refers to a polymer of amino acid residues linked together by a peptide bond. The term is meant to include proteins and polypeptides of any size, structure or function. Typically, however, a protein is at least 10 amino acids long. A protein may be naturally occurring, recombinant, or synthetic, or any combination there of. A protein may also be a fragment of a naturally occurring protein. A protein may be a single molecule or may be a multi-molecular complex. The term protein may also apply to amino acid polymers in which one or more amino acid residues is an artificial chemical analogue of a corresponding naturally occurring amino acid. An amino acid polymer in which one or more amino acid residues is an "unnatural" amino acid not corresponding to any naturally occurring amino acid is also encompassed by the use of the term "protein" herein.

The term "protein fragment", as used herein, refers to a peptide that is a portion of another protein. For instance, a protein fragment may be a peptide obtained by digesting a full-length protein. A protein fragment typically comprises at least two amino acids.

The terms "photocrosslinking" and "photoactive" refer to a compound having a photofunctional group that reacts in the presence of activating light resulting in crosslinking. The photoactive group may include, without limitation, azide, diazirine, or nucleoside analogs. The activating light can be of visible or non-visible wavelengths. In some embodiments, the activating light is ultraviolet (UV) light.

The terms "amino acid side group" refer to a substitution group comprising an amino acid moiety, wherein the amino acid moiety may be from a natural amino acid or synthetic (non-natural) amino acid. A natural amino acid includes all naturally occurring amino acids, including all standard and non-standard amino acids. Non-limiting examples of amino acids include non-limiting example: Agmatine, Beta Alanine, Arginine, Asparagine, Aspartic Acid, Cysteine, Glutamine, Glutamic Acid, Glycine, Histidine, Isoleucine, Leucine, Lysine, Methionine, PhenylBeta Alanine, Proline, Serine, Threonine, Tryptophan, Tyrosine, and Valine. A synthetic amino acid is a natural amino acid with one or more atoms or bonds replaced or substituted.

The terms "crosslink", "crosslinking", "crosslinked", and grammatical derivatives thereof refer to the covalent bonding or bonds between molecules or solid supports.

The term "alkyl", as used herein, refers to a branched, unbranched, or cyclic hydrocarbon having, for example, from 1 to 20 carbon atoms, and often 1 to about 12, 1 to about 6, or 1 to about 4 carbon atoms. Examples include, but are not limited to, methyl; ethyl; 1-propyl; 2-propyl; 1-butyl; 2-methyl-1-propyl; 2-butyl; 2-methyl-2-propyl (t-butyl); 1-pentyl; 2-pentyl; 3-pentyl; 2-methyl-2-butyl; 3-methyl-2-butyl; 3-methyl-1-butyl; 2-methyl-1-butyl; 1-hexyl; 2-hexyl; 3-hexyl; 2-methyl-2-pentyl; 3-methyl-2-pentyl; 4-methyl-2-pentyl; 3-methyl-3-pentyl; 2-methyl-3-pentyl; 2,3-dimethyl-2-butyl; 3,3-dimethyl-2-butyl; hexyl; octyl; decyl; dodecyl; and the like. An alkyl group can be unsubstituted or substituted.

The term "hydrocarbyl", as used herein, means that the group concerned is primarily composed of hydrogen and carbon atoms and is bonded to the remainder of the molecule via a carbon atom, but it does not exclude the presence of other atoms or groups in a proportion insufficient to detract from the substantial hydrocarbon characteristics of the group. The hydrocarbyl group is preferably composed of only hydrogen and carbon atoms. The hydrocarbyl group is preferably an aliphatic group, more preferably alkyl or alkylene group, especially alkyl groups, which may be linear or branched.

The term "aryl" means, unless otherwise stated, a polyunsaturated, aromatic, hydrocarbon substituent which can be a single ring or multiple rings (including but not limited to, from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a hteroatom. Non-limiting examples of aryl and heteroaryl groups include phenyl, 1-napththyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl.

The term "Mass Tag", as used herein, refers to any chemical moiety that (i) has a fixed mass, (ii) is affixable to peptide or protein, and (iii) whose mass is determinable using mass spectrometry. Mass tags include, for example, chemical moieties, such as small organic molecules, and have masses that range, for example, from 100 Da to 2500 Da.

Throughout the description, where compositions are described as having, including, or comprising specific components, or where processes are described as having, including, or comprising specific process steps, it is contemplated that compositions of the present invention also consist essentially of, or consist of, the recited components, and that the processes of the present invention also consist essentially of or consist of, the recited processing steps. Furthermore, it should be understood that the order of steps or order for performing certain actions are immaterial as long as the invention remains operable. Moreover, two or more steps or actions may be conducted simultaneously.

BRIEF DESCRIPTION OF THE FIGURES

FIG. 1 illustrates the structures of reversible crosslinking reagents having Formula (I), (II), (III), and (IV).

FIG. 2 illustrates the general method for covalently capturing an interaction between two proteins.

FIG. 3 illustrates a general method for isolating crosslinked products.

FIG. 4 illustrates a general method for purifying crosslinked products.

FIG. 5 illustrates a multi-dimensional detection method based on the reversible linking chemistry.

FIG. 6 illustrates the structure of a single multifunctional tag and its usage for multi-dimensional detection.

FIG. 7 illustrates the general chemical structures of photocrosslinking reagents (DTDA, PEAS, and NETDB) used in Khorana's lab for studying protein-protein interactions.

FIG. 8 is a schematic example of the photocrosslinking strategy for studying protein-protein interactions using rhodopsin as a model system. Single cysteine substitution mutants of rhodopsin arc dcrivatized with sulfhydryl-specific crosslinking reagents, NETDB, that, on photolysis, yield the reactive carbene intermediates leading to the crosslinking of transducin. An example of the yield of crosslinking between rhodopsin K248C and transducin (T) is on the order of 1%. The sites of crosslinks in T are identified by a strategy involving the following steps: (1) derivatization of all of the free cysteines in the crosslinked proteins with N-ethylmaleimide; (2) reduction of the disulfide bond linking the two proteins and isolation of all of the resulting T derivatives carrying the crosslinkcd moiety with a free SH group; (3) Texas Red fluorescence-labeling of the sulfhydryl crosslinked products through thioether formation; (4) degradation of the resulting T derivatives using immobilized trypsin and isolation of fluorescence tagged T peptides by C18 reverse phase HPLC; and (5) identification of the isolated peptides by matrix-assisted laser desorption/ionization time-of-flight (MALDI-TOF) MS.

FIG. 9 are exemplary photographs of gel electrophoresis illustrating the identification of the binding subunit of transducin involved in the interactions between rhodopsin mutants (A241C and K67) and transducin. ID4-Sepharose without bound rhodopsin was used as a control and the derivatization and crosslinking conditions were identical in the case of A241C and K67C. The gels containing crosslinked samples were separated and visualized by fluorescence imaging. In the marker (lane 1), only the pre-stained protein with red dye was visible (63.8 KDa). Texas Red maleimide or solvent-modified Texas Red migrated to the very front of the gel. Only one major band was observed, at roughly 40 KDa for A241C (lane 2) and K67C (lane 3), corresponding to the transducin alpha subunit.

FIG. 10 depicts exemplary synthetic routes to heterobifunctional photocrosslinking reagents having a peptide spacer and reversible oxime bond.

FIG. 11 depicts exemplary synthetic routes to photocrosslinking agents having ethylene glycol and methylene spacer.

FIG. 12 depicts exemplary synthetic routes to cleavable oxime-linked photocrosslinking agents having ethylene glycol and methylene spacer.

FIG. 13 depicts exemplary synthetic routes to cleavable disulfide linked photocrosslinking agents having ethylene glycol or methylene spacer.

FIG. 14 depicts another exemplary synthetic route to cleavable oxime-linked photocrosslinking agents containing ethylene glycol or methylene spacer.

FIG. 15 is an exemplary HPLC data of the NHS ester formation for N-phthalimidooxyacetic acid and 4-(3-Trifluoromethyl-3H-diazirin-3-yl)benzoic Acid.

FIG. 16 is an exemplary HPLC data of the NHS ester coupling reaction for compound J1, J2, J3.

FIG. 17 is an exemplary HPLC data of purified compounds k1 and 11.

FIG. 18 depicts exemplary synthetic routes to amide bond linked multi-functional protein labeling agent on a cleavable solid support.

FIG. 19 is a schematic example of the isolation and/or purification of crosslinked peptide fragments having an aminooxy group.

DETAILED DESCRIPTION OF THE INVENTION

In its simplest sense, the invention is to detect and characterize a protein-protein interaction via the covalent crosslinking approach, for example, through the detection of covalent protein complexes using gel electrophoresis or identification of the crosslinking sites using mass spectroscopy. The present invention provides novel chemical compositions of strategically designed reversible crosslinking reagents suitable for studying protein-protein interactions and for mapping the interaction sites at the molecular level. The present invention also provides methods for the isolation, purification, and/or enrichment of crosslinked peptide fragments based on the novel reversible linker. Furthermore, the present invention provides novel protein tagging reagents for multi-dimensional detection. A combination of those methods using reversible crosslinking reagents leads to improved general approaches for mapping the contact sites of a protein-protein interaction in a convenient, accurate, and sensitive way.

Methods of the present invention have certain advantages, including (i) the ability to study protein-protein interactions of a non-purified protein, such as in a cell; (ii) detection of protein-protein interactions at the sub-picomole range; and (iii) that mapping the contact sites of the interactions can eventually lead to the structures of the complexes.

Previous technologies for identifying the sites of crosslinking developed in Khorana's lab and others rely heavily on inefficient nitrene-generating photocrosslinking reagents and non-covalent avidin/biotin interactions for capturing the crosslinked peptide fragments (Cai el. al. *Proc. Natl. Acad. Sci. USA*. 2001, 98, 4877-4882). In this approach, monocysteine mutants of rhodopsin on the cytoplasmic face form the starting points for attachment of the crosslinking reagents. A bifunctional crosslinking reagent with cleavable sulfhydryl to connect rhodopsin and a nitrene-generating photoactivable reagent for covalently crosslinking transducin is used. The photocrosslinked products can be digested by trypsin and analyzed by mass spectrometry. More specifically, the identification of the sites of crosslinks in transducin (T) involves the following steps: (i) derivatization of all of the free cysteines in the crosslinked proteins with N-ethylmaleimide; (ii) reduction of the disulfide bond linking the two proteins and isolation of all alpha subunit of T ($T_\alpha$) species carrying the crosslinked moiety with the free SH group; (iii) derivatization of SH with biotin analog; (iv) trypsin degradation of the resulting $T\alpha$ derivatives and isolation of $T_\alpha$ peptides by avidin-agarose chromatography; and (v) identification of the isolated peptides by MALDI-TOF MS. Nitrene photocrosslinking reagent is known for its inefficient photolysis and non-specific labeling. Data obtained through nitrene crosslinking may not be reliable. When peptide fragments are captured using biotin/avidin, a large excess of biotin (milligram scale) is used for eluting the peptide fragments (picomole range). The presence of a million-fold hydrophobic biotin results in high background signal during the mass spectrometric analysis. As a result, little or no structural data has been obtained using this approach.

Further improvement of this approach by Y. Huang in Khorana's lab focused on a solution-based purification strategy for peptide fragments and advanced MS/MS fragmentation to determine the contact sites (Huang, Y., Khorana, H. G. (2003) "Mapping of Contact Sites in Interaction between Transducin and Light-Activated Rhodopsin." 17th Symposium of the Protein Society, July 26-30, Boston, Mass.). Thus, a Texas Red maleimide was used for derivatization of SH after crosslinking. Fluorescence tagging allows the direct visualization of crosslinked subunits and detection of the derivatized peptide fragments after HPLC purification. Due to the limited amount of sample, however, the data generated so far are either confusing or difficult to interpret.

Other disadvantages limit the power of the photocrosslinking approach. For example, the first protein to be studied has to contain a single sulfhydryl group, which is generally accomplished through cysteine mutagenesis. Cysteine is a natural amino acid and exists in almost all proteins. Multiple Cys mutations may result in misfolded protein or may affect the activity of folded protein. Additionally, the first protein to be analyzed has to be purified and non-covalently attached to a solid support through antibody for the convenience of photocrosslinking and washing. Not all proteins can be expressed in large quantities and purified through affinity columns. For example, most of the G-protein coupled receptors do not yet have an affinity purification system established. Furthermore, due to the presence of natural Cys in the second protein to be crosslinked, an extra step is required for blocking these Cys amino acids, leading to further sample loss and complicating the final data analysis.

Another disadvantage of the above approach is a stable linkage generated after derivatization of sulfhydryl containing photocrosslinked proteins. The proteins or peptides can only be subjected to a single detection method and the sample cannot be reused. This is a potential problem for low sample quantities. For example, in a typical rhodopsin and transducin crosslinking experiment, only a few picomoles of crosslinked product can be obtained from a few nanomoles of the starting material, rhodopsin.

Another disadvantage of this approach is the limited variety of phenyldiazirine-based reagents. Thus, a complete structural illustration is impossible based on a single phenyldiazirene reagent.

The present invention provides methods and compositions for studying interactions between proteins that are more versatile than the above approach. The present invention provides collective novel reversible photocrosslinkers for systematically mapping the contact sites of interactions. Additionally, the present invention provides a novel method for isolating and/or purifying crosslinked products through reversible linkage. Furthermore, the present invention provides a method for sample enrichment that allows supersensitive detection. Overall, these reagents and the improved methods permit the establishment of a novel platform for assaying protein-protein interactions and/or for characterizing known and novel protein-protein interactions. For example, the present invention provides a method of assaying protein-protein interactions in a collection of cells in which individual cells express the protein of interest that incorporate a natural or artificial amino acid at a specific position that allows the introduction of crosslinking reagent in vivo. This amino acid can be Cys or an amino acid analog containing a functional group orthogonal to a natural amino acid, such as an aldehyde group. Therefore, the present invention may be used to identify those proteins that interact with the protein of interest and the amino acids in contact with the proteins. By varying the position of the amino acids and/or using systematically designed crosslinking reagents, the method allows the complete mapping of the contact sites between two proteins.

Additionally, the present invention may be used to characterize known and novel protein-protein interactions under a variety of chemical, genetic, nutritional and environmental conditions. For example, the effects of molecules or chemicals that enhance or disrupt protein-protein interactions may be assayed. Also, protein-protein interactions may be assayed in cell lines with different genetic backgrounds, such as the presence or absence of oncogenes.

Furthermore, the present invention may be used to characterize known protein-protein interactions in vitro using purified protein or part of the tissues and cells containing the protein of interest. For example, the protein may be genetically modified to contain a single functional group for incorporating the photo- or chemically reactive group.

In one aspect, the invention generally relates to a crosslinking reagent having the Formula (I)

FG2-SP1-W  (I)

wherein

FG2 is a chemical functional group selected from the group consisting of an aminooxy group, an aldehyde group, a keto group, a hydrazide group, a semicarbazide group, and a thiosemicarbazide group;

SP1 is a spacer group selected from the group consisting of a bond, a substituted or unsubstituted ($C_1$-$C_{24}$) alkyl group, a substituted or unsubstituted ($C_1$-$C_{24}$) heteroalkyl group, a polyethyleneglycol group, a polyalcohol group, a polyamine group, a polyester group, a polyphosphodiester group, a peptide, and a peptidomimetics group; and W is a chemical- or photocrosslinking group selected from the group consisting of an aryl ketone group, an azide group, a diazo group, a diazirene group, a ketene group, an olefin group, a dicarbonyl group, an epoxide group, an organosilane group, an isothiocyanate group, an isocyanate group, an acyl azide group, an ester group, a sulfonyl chloride group, a carbonate group, an imidoester group, an anhydride group, a haloacetyl group, an alkyl halide group, a maleimide group, a vinylsulfone group, a thioester group, a disulfide group, and a sulfhydryl group, In some embodiments, the ester group is selected from N-hydroxylsuccinimide esters and fluorophenyl ester groups. W may be a substituted or unsubstituted trifluoromethyl phenyl diazirine group. In certain embodiments, W is a perfluorinated phenyl azide group. In certain other embodiments, W is a haloacetyl group, an alkyl halide group, a maleimide group, or an N-hydroxylsuccinimide ester group.

Examples of the crosslinking reagents of the invention include those having the structural Formula (A):

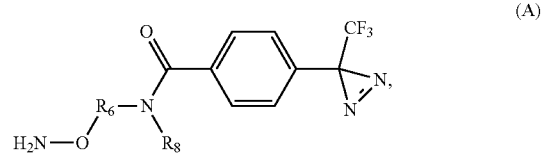

wherein $R_6$ is selected from —$(CH_2)_n$— and —$O(CH_2CH_2)_n$—, wherein each n is an integer independently selected from between 1 and 16 inclusive. $R_8$ is H, or an alkyl group.

Examples of the crosslinking reagents of the invention include those having the structural Formula (B):

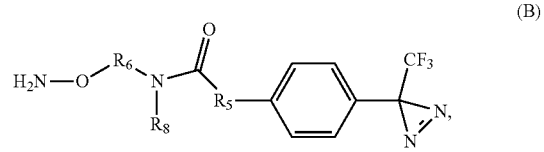

wherein each of $R_5$ and $R_6$ are independently selected from —$(CH_2)_n$— and —$O(CH_2CH_2)_n$—, wherein each n is an integer independently selected from between 1 and 16 inclusive. $R_8$ is H, or an alkyl group.

Examples of the crosslinking reagent of the invention include those having the structural Formula (C):

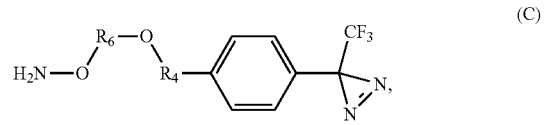

wherein each of $R_5$ and $R_6$ are independently selected from —$(CH_2)_n$— and —$(CH_2CH_2)_n$—, wherein each n is an integer independently selected from between 1 and 16 inclusive.

Examples of the crosslinking reagent of the invention include those having structural Formula (D):

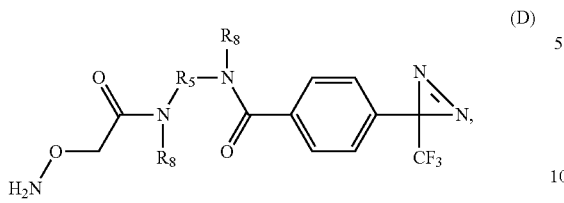

(D)

wherein $R_5$ is selected from —$(CH_2)_n$— and —$O(CH_2CH_2)_n$—; wherein each n is an integer independently selected from between 1 and 16 inclusive; $R_8$ is H, or an alkyl group.

Examples of the crosslinking reagent of the invention include those having the structural Formula (E):

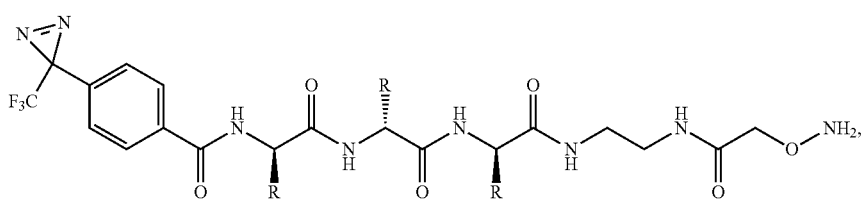

(E)

wherein each R is independently an amino acid side group.

In another aspect, the invention generally relates to a crosslinking reagent having the Formula (II)

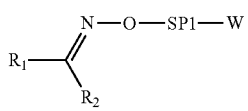

(II)

wherein $R_1$ and $R_2$ are independently a H, an alkyl group, or an aryl group;

SP1 is a spacer group selected from the group consisting of a bond, a substituted or unsubstituted $(C_1$-$C_{24})$ alkyl group, a substituted or unsubstituted $(C_1$-$C_{24})$ heteroalkyl group, a polyethyleneglycol group, a polyalcohol group, a polyamine group, a polyester group, a polyphosphodiester group, a peptide, and a peptidomimetic group; and W is a chemical or photo crosslinking group selected from the group consisting of an aryl ketone group, an azide group, a diazo group, a diazirene group, a ketene group, an olefin group, a dicarbonyl group, an epoxide group, an organosilane group, an isothiocyanate group, an isocyanate group, an acyl azide group, an N-hydroxylsuccinimide ester group, a fluorophenyl ester group, a sulfonyl chloride group, a carbonate group, an imidoester group, an anhydride group, a haloacetyl group, an alkyl halide group, a maleimide group, a vinylsulfone group, a thioester group, a disulfide group, and a sulfhydryl group.

In certain embodiments, W is a substituted or unsubstituted trifluoromethyl phenyldiazirine group. In some embodiments, W is a perfluorinated phenyl azide group. In some embodiments, W may be a haloacetyl group, an alkyl halide group, a maleimide group, or an N-hydroxylsuccinimide ester group.

Examples of the crosslinking reagents of the invention include those having the structural Formula (F)

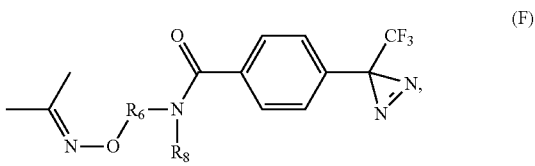

(F)

wherein $R_6$ is selected from —$(CH_2)_n$— and —$O(CH_2CH_2)_n$—; and wherein each n is an integer independently selected from between 1 and 16 inclusive; $R_8$ is H, or an alkyl group.

Examples of the crosslinking reagents of the invention include those having the structural Formula (G):

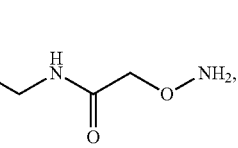

(G)

wherein each of $R_5$ and $R_6$ are independently selected from —$(CH_2)_n$— and —$O(CH_2CH_2)_n$—, wherein each n is an integer independently selected from between 1 and 16 inclusive.

Examples of the crosslinking reagents of the invention include those having the structural Formula (H):

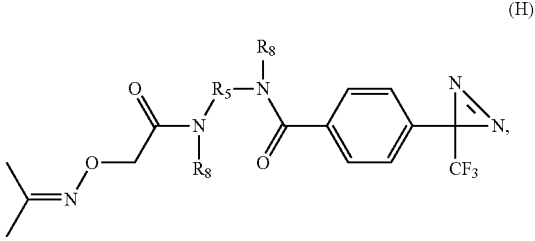

(H)

wherein $R_5$ is selected from —$(CH_2)_n$— and —$O(CH_2CH_2)_n$—; and wherein each n is an integer independently selected from between 1 and 16 inclusive; $R_8$ is H, or an alkyl group.

Examples of the crosslinking reagents of the invention include those having the structural Formula (I'):

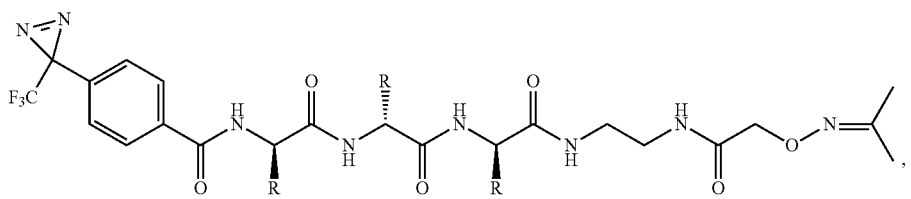

wherein each R is independently selected from an amino acid side group.

In yet another aspect, the invention generally relates to a crosslinking reagent having the formula (III)

V—SP2-L-SP1-W    (III)

wherein
V is a chemical crosslinking group selected from the group consisting of an isothiocyanate group, an isocyanate group, an acyl azide group, an ester group, a sulfonyl chloride group, a carbonate group, an imidoester group, an anhydride group, a haloacetyl group, an alkyl halide group, a maleimide group, a vinylsulfone group, and a thioester group;
W is a chemical- or photo-crosslinking group selected from the group consisting of an aryl ketone group, an azide group, a diazo group, a diazirene group, a ketene group, an olefin group, a dicarbonyl group, an epoxide group, an organosilane group, an isothiocyanate group, an isocyanate group, an acyl azide group, an ester group, a sulfonyl chloride group, a carbonate group, an imidoester group, an anhydride group, a haloacetyl group, an alkyl halide group, a maleimide group, a vinylsulfone group, a thioester group, a disulfide group, and a sulfhydryl group;
each of SP1 and SP2 is independently a spacer group selected from the group consisting of a bond, a substituted or unsubstituted ($C_1$-$C_{24}$) alkyl group, a substituted or unsubstituted ($C_1$-$C_{24}$) heteroalkyl group, a polyethyleneglycol group, a polyalcohol group, a polyamine group, a polyester group, a polyphosphodiester group, a peptide, and a peptidomimetics group; and
L is an oxime bond.

In certain embodiments, W is a substituted or unsubstituted trifluoromethyl phenyldiazirine group. In some embodiments, W is a perfluorinated phenyl azide group. In some embodiments, W may be a haloacetyl group, an alkyl halide group, a maleimide group, or an N-hydroxylsuccinimide ester group.

Examples of the crosslinking reagents of the invention include those having the structural Formula (J)

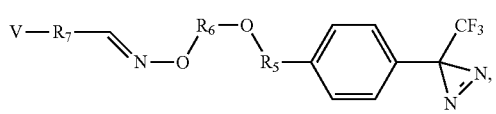

wherein V is a haloacetyl group, an alkyl halide group, a maleimide group, or an N-hydroxylsuccinimide ester group; each of $R_6$ and $R_7$ is independently selected from —$(CH_2)_n$— and —$O(CH_2CH_2)_n$—; and wherein each n is an integer independently selected from between 1 and 16 inclusive; $R_8$ is H, or an alkyl group.

Examples of the crosslinking reagents of the invention include those having the structural Formula (J')

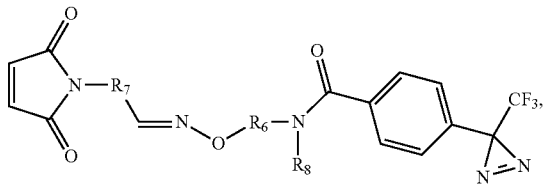

wherein each of $R_6$ and $R_7$ is independently selected from —$(CH_2)_n$— and —$O(CH_2CH_2)_n$—; and
wherein each n is an integer independently selected from between 1 and 16 inclusive; $R_8$ is H, or an alkyl group.

Examples of the crosslinking reagents of the invention include those having the structural Formula (K):

(K)

wherein V is a haloacetyl group, an alkyl halide group, a maleimide group, or an N-hydroxylsuccinimide ester group; each of $R_5$, $R_6$ and $R_7$ is independently selected from —$(CH_2)_n$— and —$O(CH_2CH_2)_n$—; and wherein each n is an integer independently selected from between 1 and 16 inclusive.

Examples of the crosslinking reagents of the invention include those having the structural Formula (K'):

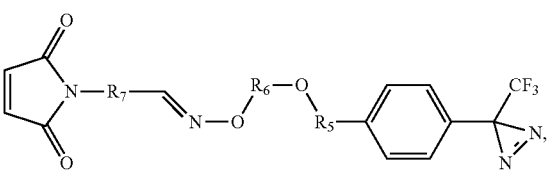

wherein each of $R_5$, $R_6$, and $R_7$ are independently selected from —$(CH_2)_n$— and —$O(CH_2CH_2)_n$—, wherein each n is an integer independently selected from between 1 and 16 inclusive.

Examples of the crosslinking reagents of the invention include those having the structural Formula (L):

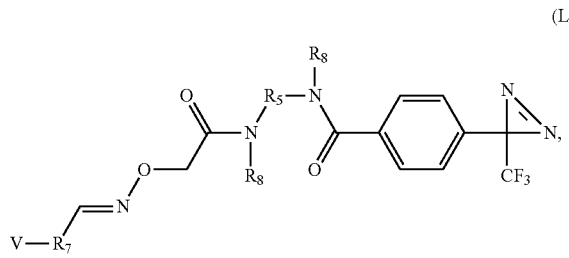
(L)

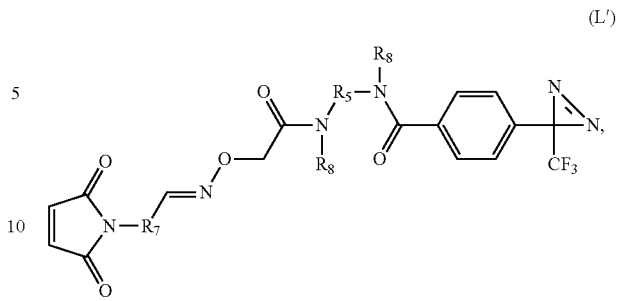
(L')

wherein V is a haloacetyl group, an alkyl halide group, a maleimide group, or an N-hydroxylsuccinimide ester group; each of $R_5$ and $R_7$ is independently selected from —$(CH_2)_n$— and —$O(CH_2CH_2)_n$—; and wherein each n is an integer independently selected from between 1 and 16 inclusive; $R_8$ is H, or an alkyl group.

Examples of the crosslinking reagents of the invention include those having the structural Formula (L'):

wherein each of $R_5$ and $R_7$ is independently selected from —$(CH_2)_n$— and —$O(CH_2CH_2)_n$—; and wherein each n is an integer independently selected from between 1 and 16 inclusive; $R_8$ is H, or an alkyl group.

Examples of the crosslinking reagents of the invention include those having the structural Formula (M):

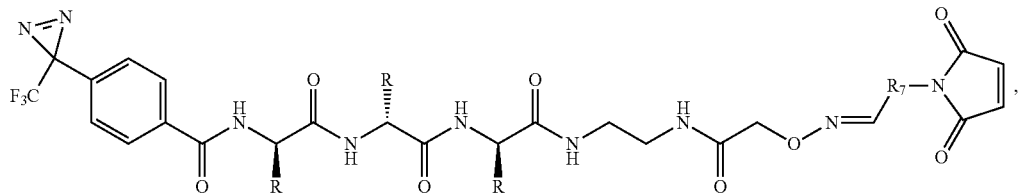
(M)

wherein V is a haloacetyl group, an alkyl halide group, a maleimide group, or an N-hydroxylsuccinimide ester group; each R is independently an amino acid side group.

Examples of the crosslinking reagents of the invention include those having the structural Formula (M'):

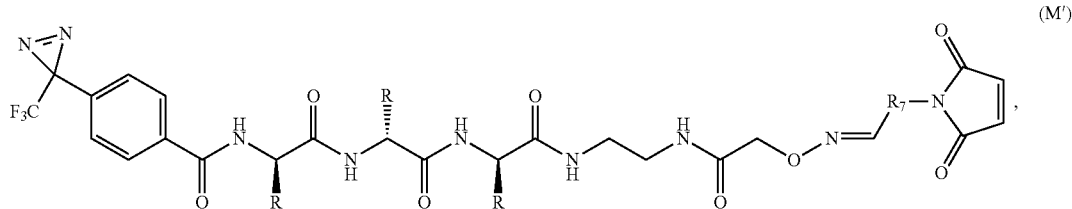
(M')

wherein each R is independently selected from an amino acid side group.

In yet another aspect, the invention generally relates to a reagent for protein or peptide labeling having the formula (V):

$$S\text{—}Y\text{-}T_1\text{-}T_2 \ldots T_n\text{-}Z \quad (V)$$

wherein
S is a solid support;
Y is a cleavable linkage;
$T_1, T_2, \ldots T_n$ is a tagging molecule;
n is an integer selected from 1, 2, 3, 4, 5, and 6; and
Z is a crosslinking group capable of reacting with an aldehyde, a keto, or an aminooxy.

T may be a mass tag, a fluorescent tag, a hydrophobic moiety, an epitope tag, a radioactive moiety, a chromophore moiety, a UV active moiety or chemiluminescent tag.

In certain embodiments, Y and $T_1, T_2, \ldots Z$ are covalently connected through an amide bond, a C—C bond, a C—O bond, or a C—N bond.

In certain embodiments, Z is an aminooxy group.

Examples of the reagent include the compound having the structural Formula (N):

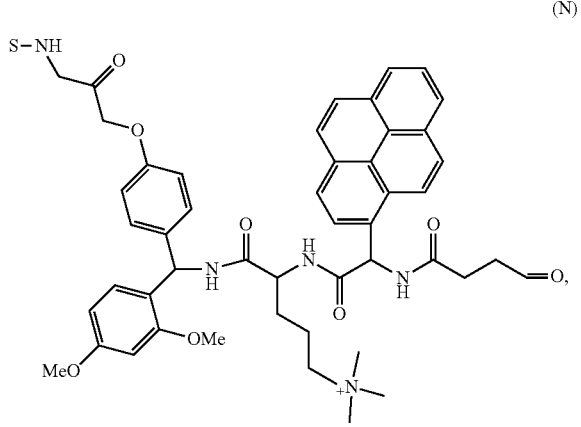 [SMILES: COc1ccc(C(NC(=O)C(CCC[N+](C)(C)C)NC(=O)C(NC(=O)CCC=O)c2ccc3ccc4cccc5ccc2c3c45)c2ccc(OCC(=O)CNS)cc2)c(OC)c1]

(N)

wherein S is a solid support.

A. Reversible Crosslinking Reagents

Different types of reversible crosslinking reagents were designed for probing the protein-protein complex and for the characterization of the interaction sites at the molecular level. FIG. 1 illustrates the structures of reversible heterobifunctional crosslinking reagents with Formulas (I), (II), (III), and (IV).

Reversible crosslinking reagent (III) comprises: (i) a chemical crosslinking group (V) that can react with the protein of interest to form a stable linkage; (ii) a reversible linker (L) for the isolation, purification, and enrichment of crosslinked products, where L can be formed and unformed or broken apart upon particular chemical treatment, and upon cleavage of the L bond, functional group FG2 and functional group FG1 are generated; (iii) a chemical- or photocrosslinking group (W) that can crosslink the interacting protein partner; (iv) a first spacer group (SP1) to connect L and W; and (v) a second spacer group that connects L and V (SP2). Reversible crosslinking reagent III is useful for derivatizing native proteins or Cys-mutated proteins while taking advantage of non-disulfide linkage for post-processing the crosslinked sample.

In certain embodiments, L is an oxime, hydrazone, semicarbazone, or thiosemicarbazone bond. In the case of an oxime bond, the linkage can be cleaved under weak basic conditions, such as a pH of 8-10, to generate FG1 and FG2. In a preferred embodiment, FG2 is an aldehyde or ketone group and FG1 can be an aminooxy group. Alternatively, FG2 can be an aminooxy group and FG1 can be an aldehyde or ketone group. FG1 and FG2 can react at slightly acidic conditions, such as a pH of 4-6.8, to easily regenerate the oxime linkage. In the case of a hydrozone linkage, the linkage can be cleaved under weak basic conditions, such as a pH of 8-10, to generate FG1 and FG2. In a preferred embodiment, FG2 is an aldehyde or ketone group and FG1 can be a hydrazine or hydrazide. Alternatively, FG1 can be a hydrazine or hydrazide and FG2 can be an aldehyde or ketone group. FG1 and FG2 can react at weak acidic conditions, such as a pH of 4-6.8, to easily regenerate the hydrazone linkage.

In some embodiments, SP1 and SP2 are independent spacer groups with different chain lengths that allow the systematic study of the distance between the contact sites. For example, a single amino acid can be derivatized with different lengths of crosslinking reagent and subjected to the same crosslinking conditions, sample processing, and characterization. Analyzing data from different crosslinking reagents can give insight into the structure of the contact sites. SP1/SP2 can have different physical properties to allow the selection of the most suitable photocrosslinking reagents for particular experiments. For example, hydrophobic methylene linker is suitable for probing membrane proteins in the lipid layer. In another example, a hydrophilic ethylene glycol linker allows a more hydrophilic photocrosslinking reagent that is suitable for probing protein-protein interactions in the water layer. In another example, a short segment peptide backbone can also be included. To comply with the enzyme digestion, D-amino acids or unnatural amino acids can be used instead of L-amino acids. By altering the amino acids, different backbone properties can be constructed. Because amino acids, by their nature, are more related to protein itself, they should not interfere too much with the interactions between two proteins. In another embodiment, SP1 and SP2 may be only a bond or a substituted or unsubstituted ($C_1$-$C_{24}$) hetcroalkyl group, polyalcohol group, polyamine group, polyester group, or polyphosphodiester group.

In some embodiments, W is a chemical- or photocrosslinking group selected from the among aryl ketones; azides; diazo compounds; diazirenes; ketenes; olefins; dicarbonyl groups; epoxides; organosilanes; isothiocyanates; isocyanates; acyl azides; active esters, for example, but not limited to, N-hydroxylsuccinimide esters and fluorophenyl esters; sulfonyl chlorides; carbonates; imidoesters; anhydrides; haloacetyl and alkyl halide derivatives: maleimides; vinylsulfone derivatives; thioesters; disulfides; and sulfhydryl group.

In a preferred embodiment, a photoreactive group is a phenyldiazirine-based compound. Phenyldiazirine-based compounds generally undergo photolysis at roughly 360 nm, and the generated carbene can efficiently insert into C—H bonds within picoseconds. Due to the electron-withdrawing effect of the trifluoromethyl group, the diazo-isomer that is formed is very stable and does not generate side products under normal labeling conditions, resulting in very efficient and specific covalent crosslinking. In another preferred embodiment, a photoreactive group is a fluorinated arylazide. Perfluoroaryl azide undergoes intermolecular photoreactions involving the singlet nitrene. Unlike the simple aryl azide, perfluoroaryl azide is a very efficient photocrosslinker without side reactions.

In some embodiments, V is a chemical crosslinking group that can react with functional groups in the protein of interest to form a stable linkage. For example, V can be a thiol-reactive functional group, such as maleimide, haloacetyl, or an alkyl halide derivative. In this case, Cys mutagenesis can still be used to introduce the crosslinking reagent at a specific site, whereas the post-purification of crosslinked products uses other chemistry. V can also be an amine reactive group, such as isothiocyanate; isocyanates; active esters, for example, but not limited to, N-hydroxylsuccinimide ester and fluorophenyl ester; sulfonyl chlorides; carbonates; imidoesters; and anhydrides.

The reversible linkage can also be the bond connecting the protein of interest and crosslinking reagent, as shown in Formulas (I) and (II) (FIG. 1). In this case, an unnatural amino acid or comparable functional group, such as an aldehyde or keto, has to be introduced to the protein of interest first.

Crosslinking reagent (I) comprises (i) a functional group (FG2) capable of forming a reversible linkage, (ii) a chemical- or photocrosslinking group (W) that can crosslink the interacting protein, and (iii) a spacer (SP1) to connect L and W. In a preferred embodiment, FG2 is an aminooxy, aldehyde, keto, hydrazide, scmicarbazide, or thiosemicarbazide.

In a particular embodiment, a crosslinking reagent can have Formula (II), where the reversible linkage is an oxime, hydrazone, sernicarbazone, or thiosemicarbazone and is connected directly to a hydrocarbon or substituted aromatic ring. The hydrocarbon group can be easily exchanged with another molecule to allow the incorporation of the reversible linkage; for example, a methyl group that connects to a reversible oxime bond. Upon cleavage or exchange, an acetone molecule is generated.

In another embodiment, a photoactivable compound can have Formula (IV), wherein a photocrosslinking moiety is linked by a spacer group (SP') and disulfide bond to substitute benzene or heterocycle capable of generating a chromophore after being released from the compound. For example, the releasable group can be a nitrobenzoic group or its analog. The disulfide bond nitrobenzoic group has a $\lambda$max at 325 nm. However, the released dianion chromophore has a maximum absorption at 409.5 nm, and the extinction coefficient at 412 nm can be used to quantify the extent of protein labeling (Jocelyn, P. C. *Methods in Enzymology.* 1987, 143, 44 67). In another example, the releasable group can be a 2-thiol-pyridyl group or its analog. Upon release, 2-thiol pyridine can be used to quantify the extent of protein labeling.

B. Method for Covalently Capturing an Interaction between Two Proteins

FIG. 2 Illustrates an embodiment of a general approach for capturing an interaction between two proteins using crosslinking reagent III as an example. The method comprises (a) providing (i) the first protein to be assayed (protein 1) that containing functional groups, wherein functional group is sulfhydryl group, or aldehyde, or keto, or aminooxy, or hydrazide, or amine. Functional groups can be natural or introduced through mutagenesis, or modified tRNA analog, or chemical modification; Protein 1 is in a cellular environment, in a mixture of proteins, in a membrane, or purified; (ii) reversible crosslinking reagent (I), (II), (III), or (IV); (b) combining protein 1 with a reversible crosslinking agent under conditions that permit the incorporation of a crosslinking group into protein 1; (c) providing an interacting protein partner (protein 2) and combining protein 2 with protein 1 under conditions in which protein 1 interacts with protein 2, bringing it into reactive proximity of the crosslinking group and protein 2 when photolysis or chemical conditions are applied to form a covalently stabilized protein complex; and (d) incubating the crosslinked protein complex under cleavage conditions that break off the reversible linker and releases protein 1 and the crosslinked protein 2 containing FG2. Further characterization of the crosslinked protein 2 can reveal the sites of interaction.

In certain embodiments, the first protein may be a soluble protein or a membrane-bound protein, such as a transmembrane receptor, particularly a GPCR. The second protein may be a soluble protein, a membrane-bound protein, or a membrane-associated protein, particularly a G-protein.

In certain other embodiments, the first protein may be attached to a solid support through non-covalent interaction or covalent crosslinking. The support matrix comprises dextran, agarose, silica, synthetic polymer or one of these molecules covalently coupled to an antibody, ligand, or epitope tag.

C. Methods for Isolating Crosslinked Products

In certain preferred embodiments, reversible linker L can be cleaved to allow the incorporation of a solid support for purification purposes. This purification handle can be incorporated immediately after the crosslinking to allow the separation of crosslinked proteins from other non-covalently crosslinked proteins. This step is particularly useful when the protein-protein interactions occur in a mixture of proteins, membrane, or a living cell. Early isolation of crosslinked proteins leads to a clean sample for enzymatic or chemical digestion.

FIG. 3 illustrates an embodiment of a method for the isolation of crosslinked protein through a solid support. The method comprises (a) providing (i) a solid support bearing a functional group (FG1), wherein FG1 is capable of reacting with FG2 to form a reversible linkage, and (ii) a mixture of non-crosslinked proteins and crosslinked protein 2 bearing FG2; (b) combining the mixture of non-crosslinked and crosslinked proteins with a solid support under conditions that allow the formation of a reversible linkage through the reaction of FG1 and FG2; (c) physically isolating the solid supported crosslinked protein 2 from non-crosslinked proteins by filtration or the like; (d) incubating the solid supported protein 2 under cleavage conditions that release and regenerate the crosslinked protein 2 bearing FG2;(e) physically isolating the crosslinked protein bearing FG2 from the solid support by filtration or the like; (f) chemically, enzymatically, or a combination of both digesting the crosslinked protein 2 to obtain a mixtures of peptides; (g) providing another solid support bearing FG1 and mixing it with digested peptides under conditions that allow the formation of a reversible linkage through the reaction of FG1 and FG2; (h) physically isolating the solid supported crosslinked peptides bearing FG2 from non-crosslinked peptides by filtration or the like; (i) incubating the solid supported crosslinked peptides in a minimum amount of cleavage buffer to regenerate the crosslinked peptides bearing FG2; and (j) physically isolating the crosslinked peptides from the solid support by filtration or the like.

In another approach, crosslinked proteins can be enzymatically or chemically digested first to generate protein fragments, and then the purification handle can be incorporated after the crosslinking to allow the separation of the crosslinked proteins from other non-covalently crosslinked proteins (FIG. 3, bypass steps a-f). This simplified method is useful when the protein-protein interactions are done using purified protein. The method comprises (a) chemically, enzymatically, or a combination of both digesting the crosslinked protein 2 to obtain a mixtures of peptides; (b) providing another solid support bearing FG1 and mixing it with digested peptides under conditions that allow the formation of a reversible linkage through the reaction of FG1 and FG2; (c) physically isolating the solid supported crosslinked peptides bearing FG2 from non-crosslinked peptides by filtration or the like; (d) incubating the solid supported crosslinked peptides in a minimum amount of cleavage buffer to regenerate the crosslinked peptides bearing FG2; and (e) physically isolating the crosslinked peptides from the solid support by filtration or the like.

In some cases, the selected solid support does not interfere with the digestion process. The solid support crosslinked proteins may be subjected directly to digestion and only a single separation. The method comprises (a) providing (i) a solid support bearing a functional group (FG1), where FG1 is capable of reacting with FG2 to form a reversible linkage, and (ii) a mixture of non-crosslinked proteins and the crosslinked protein 2 bearing FG2; (b) combining the mixture of non-crosslinked and crosslinked proteins with a solid support under conditions that allow the formation of a reversible linkage through the reaction of FG1 and FG2; (c) physically isolating the solid supported crosslinked protein 2 from non-crosslinked proteins by filtration or the like; (d) chemically, enzymatically, or a combination of both digesting the crosslinked protein 2 to obtain a mixture of peptides; (e) providing another solid support bearing FG1 and mixing it with digested peptides under conditions that allow the formation of a reversible linkage through the reaction of FG1 and FG2; (f) physically isolating the solid supported crosslinked peptides bearing FG2 from non-crosslinked peptides by filtration or the like; (g) incubating the solid supported crosslinked peptides in a minimum amount of cleavage buffer to regenerate the crosslinked peptides bearing FG2; and (h) physically isolating the crosslinked peptides from the solid support by filtration or the like.

The pool of crosslinked peptides can be subjected directly to the detection methods or undergo further sample processing. For example, the pool of crosslinked peptides can be subjected directly to mass spectrometry coupled with liquid chromatography (LC). MS/MS fragmentation studies will reveal the exact amino acid position in protein 2 that can be crosslinked to protein 1. In another example, the amount of individual crosslinked peptide may not allow direct LC-MS-MS/MS analysis for detection of the contact sites at the molecular level. The crosslinked peptides can be cleaved to allow further derivatization with different tagging molecules for multi-dimensional detection as detailed in the detection method.

D. Methods for Purifying Crosslinked Products

In another embodiment, a reversible linker L can be cleaved to allow the incorporation of a soluble tagging molecule for purification purposes. Examples of tagging molecules are hydrophobic fluorescent or UV active molecules. The tagging molecule can be incorporated immediately after crosslinking to allow the separation of crosslinked proteins from other non-crosslinked proteins (FIG. 4). The method comprises (a) providing (i) a tagging molecule bearing a functional group (FG1), where FG1 is capable of reacting with FG2 to form a reversible linkage, and (ii) a mixture of non crosslinked proteins and crosslinked protein 2 bearing FG2; (b) combing the mixture of non-crosslinked and crosslinked proteins with a tagging molecule under conditions that allow the formation of a reversible linkage through the reaction of FG1 and FG2; (c) purification of the tagged crosslinked protein 2 from non-crosslinked proteins by gel electrophoresis, or chromatography , or the like; (d) chemically, or enzymatically, or a combination of both digesting the crosslinked protein 2 to obtain a mixture of peptides; and (c) purification of the tagged crosslinked peptides from non-crosslinked peptides by gel filtration, chromatography, or the like.

In another approach, crosslinked proteins can be enzymatically or chemically digested first to generate protein fragments, and then the tagging molecule can be incorporated after the crosslinking to allow the separation of crosslinked peptides from other non-covalently crosslinked peptides (FIG. 4). This simplified method is useful when the protein-protein interactions use purified proteins. The method comprises (a) chemically, enzymatically, or a combination of both digesting the crosslinked protein 2 to obtain a mixture of peptides; (b) combing a tagging molecule containing FG1 with crosslinked peptides containing FG2 under conditions that allow the formation of reversible linkage, L, through the reaction of FG1 and FG2; and (c) purification of the tagged crosslinked peptides from non-crosslinked peptides by gel filtration, or chromatography, or the like.

The tagged crosslinked peptides can be subjected directly to detection methods or undergo further sample processing. For example, the pool of crosslinked peptides can be subjected directly to mass spectrometric analysis coupled with LC. MS/MS fragmentation studies will reveal the exact amino acid position in protein 2 that can be crosslinked to protein 1. In another example, the low amount of individual crosslinked peptide may not allow direct LC-MS-MS/MS analysis for the detection of the contact sites at the molecular level. The crosslinked peptides can be cleaved to allow further derivatization with different tagging molecules for multi-dimensional detection as detailed in the detection method.

E. Detection Methods

In certain preferred embodiments, the reversible linkage can be reacted with a variety of labeling reagent comprising functional groups that form a reversible linkage with the crosslinked product. This product can be cleaved further to introduce different tagging reagents one-by-one. The tags allow the maximum utilization of the sample for analysis and is a great way to improve detection sensitivity. FIG. 5 Illustrates such scheme. In this method, the crosslinked protein or peptides containing FG2 are incubated with the first tagging molecule contacting FG1 under conditions that allow a reversible link, L, to be formed between FG1 and FG2. Then, the tagged photocrosslinked protein or peptides are subjected to the first detection based on the first tagging molecule. The crosslinked protein or peptides can be recycled by cleavage of L to regenerate FG2 and allow the incorporation of a second tagging molecule. The tagged photocrosslinked protein or peptides are subjected to the second detection based on the second tagging molecule. The crosslinked protein or peptides can be further recycled by cleavage of L to regenerate FG2 and allow detection n times.

Examples of these labeling reagents are fluorescent labeling, mass tags, and radioactive compounds. Furthermore, the labeling reagent can be an enzyme, epitope, or antibody that allows the amplification of the signals through other amplification mechanisms, such as ELISA.

Multi-dimensional detection can also be achieved through a single reaction using multiple detecting molecules already built-in to one tagging molecule. The linkage between the crosslinking reagent and the tagging molecule can be a reversible or stable linkage. FIG. 6 illustrates one embodiment of a solid supported protein or peptide tagging molecule (V) comprising (i) a solid support for isolation and/or purification (S); (ii) a cleavable linkage, Y; (iii) multiple tagging moieties $T_1, T_2, \ldots T_n$, where n is an integer and less than 6; and (iv) a crosslinking group that can react with the member selected from the following group: aldehyde, keto, aminooxy, hydrazine, hydrazide.

In some embodiments, $T_1, T_2, \ldots Z$ can be connected through an amide bond. The tagging reagent can easily be synthesized using amino acid analogous carrying a tagging moiety.

In some embodiments, the solid support can be dextran, agarose, silica, or synthetic polymer such as polystyrene.

In some embodiments, the tagging molecule can be a hydrophobic moiety that allows easy HPLC purification through a C18 column, a fluorescent moiety, or it can be the combination of hydrophobic and fluorescent molecules, such as pyrene. The tagging moiety can also be an ionization enhancing moiety to improve the sensitivity of MS/MS detection. Few groups have reported chemical methods of increasing the sensitivity of tryptic peptide detection (Tatsuya, et al. *Anal Sci.* 2002, 18, 1301-1307; Hale, et al. *Anal. Biochem.* 2000, 287, 110-117; Beardsley, et al. *Anal. Chem.* 2002, 74,1884-1890). One study reported that the trimethylation of an amino group increases the ionization of peptide efficiency 100-fold (Stewart, et al. *Rapid Commun in Mass Spectral.* 2002, 16, 1448-1453). Molecules, such as piperizine or secondary, tertiary, or quaternary amine, can be incorporated as a tagging moiety.

Multi-dimensional detection is achieved through the method illustrated in FIG. 6. The method comprises (a) combing a solid supported multifunctional tagging molecule with crosslinked proteins or peptides containing FG2 under conditions that allow the formation of linkage L' through the reaction of FG2 and Z; (b) physically isolating solid supported crosslinked proteins or peptides from non-crosslinked proteins or peptides by filtration or the like; (c) incubating the solid supported crosslinked proteins or peptides in the conditions that cleave Y; (d) physically isolating the crosslinked proteins or peptides from the solid support by simple filtration or the like; and (e) detection of the crosslinked proteins or peptides.

The following examples contain important additional information, exemplification and guidance that can be adapted to the practice of this invention in its various embodiments and equivalents thereof. Practice of the invention will be more fully understood from the following examples, which are presented here for illustrative purposes only and should not be construed as limiting in anyway.

EXAMPLES

Example 1

Synthesis of Cleavable Heterobifunctional Photocrosslinking Reagents Containing a Peptide Spacer and Reversible Oxime Bond (FIG. 10).

This example describes the synthetic routes to various lengths of photocrosslinking reagents containing a peptide spacer and cleavable oxime linker. Aminooxy functionality can be achieved by simply using an aminooxy resin during the solid phase peptide synthesis. Final cleavage of the crosslinking reagent by 95% TFA concomitantly &protects the aminooxy and provides the aminooxy-containing peptidyl photocrosslinking reagent (d). The incorporation of a maleimide group into the crosslinking agent (e) allows the crosslinking reagent to react with sulfhydryl-containing proteins. The aminooxy group can also be capped by acetone, and the acetone can easily be exchanged with other aldehyde-containing proteins (f). Direct conjugation between photocrosslinking groups with an oxime linker obtains the shortest spacer. The addition of each amino acid adds up to 3 bonds in between (approximately 4.4 Å).

Example 2

Synthesis of Photocrosslinking Reagents Containing Ethylene Glycol and a Methylene Spacer FIG. 11 describes the synthetic routes to trilluoromethyl phenyl diazirine containing various lengths of ethylene glycol or methylene linkers. Starting from the commercially available alkyl or ethylene glycol substituted benzene bromide, the trilluoromethyl phenyl diazirine analog can be synthesized following Nassal's published procedures (Nassal, M. *Liebigs Ann Chem.* 1983, 1510-1523).

Example 3

Synthesis of Cleavable Oxime-Linked Photocrosslinking Reagents Containing Ethylene Glycol and a Methylene Spacer The synthetic route to incorporate these trifluoromethyl phenyldiazirine compounds into oxime-link reagents is illustrated in FIG. 12.

Example 4

Synthesis of Cleavable Disulfide-Linked Photocrosslinking Agents Containing an Ethylene Glycol or Methylene Spacer.

FIG. 13 shows the synthetic schemes to disulfide-linked photocrosslinking agents containing ethylene glycol or methylene spacer Example 5

Synthesis of Another Type of Cleavable Oxime-Linked Photocrosslinking Reagents Containing Ethylene Glycol or Methylene Spacer FIG. 14 shows the synthetic scheme to another type of cleavable oxime-linked photocrosslinking reagents containing ethylene glycol or methylene spacer. N-phthalimidooxyacetic acid (i) can be synthesized following the literature procedure (Clave, G. et. al. *Org. Biomol. Chem.*, 2008, 6, 3065-3078). Its N-hydroxysuccimide (NHS) ester reacts with mono-Fmoc or Boc protected diamine to provide compound j. Following the same NHS ester activation method, photocrosslinking group can be easily incorporated into the system to give compound k. Removal of phthaloyl group by $NH_2NH_2$ following literature procedure affords compound I (Salo, H.; Virta, P. el al. *Bioconjugate Chem.* 1999, 10, 815-823). Compound I can be capped by acetone (n) or react with any heterobifunctional crosslinker that carrying aldehyde or ketone to obtain reagent m. The following details the experimental procedures for obtaining some of the exemplary compounds.

Synthesis of tert-butyl phthalimidooxyacctate (g): A 500 mL of round-bottomed flask, equipped with a magnetic stirring bar and a nitrogen inlet, was charged with 15.26 g (93.5 mmolc) of N-Hydroxyphthalimide, 215 mL of N-methyl pyrrolidone (NMP), and 18.84 g (136 mmole) of anhydrous $K_2CO_3$. The solution was heated to 40° C. for 10 minutes in an oil bath, and then a combined solution of tert-butyl bromoacetate (13.81 ml, 93.5 mmole) and NMP (10 mL) were added slowly via additional funnel. The reaction was stirred at 50° C. for 3 hr, and then it was cooled to RT and stirred under nitrogen for 24 hr. The progress of the reaction was checked by high pressure liquid chromatography (HPLC). The resulting reaction was transferred into a 5 L beaker containing 2 L of cold deionized water. The solid was precipitated and collected by filtration through a Büch funnel. The solid was washed twice with cold deionized water, and then transferred back into a 2 L beaker followed by addition of 1 L cold deionized water. The mixture was stirred for 5 minutes. The solid was again collected by filtration and washed with cold deionzied water. This process (mixing and washing) was repeated several times until a white solid was obtained. The solid was lyophilized to give 27.46 g of product (yield: 106%, HPLC purity: 99%).

Synthesis of N-phthalimidooxyacetic acid (h): A 250 mL of round-bottomed flask, equipped with a magnetic stir bar was charged with 14.14 g (51 mmole) of tert-butyl phthalimimidooxyacctatc and 123 mL of dry $CH_2Cl_2$. The mixture was cooled to 0° C. and then 37.85 mL (510 mmole) of TFA was added dropwise via additional funnel. After stirring for 1 hr, HPLC shows 1.5% of the starting material still in the solution. 3 mL (40.4 mmole) of TFA was added and the mixture was stirred for another 20 minutes. The mixture was then concentrated under reduced pressure and the resulting residue was co-evaporated two times with $CHCl_3$. 20 ml of water was added and the aqueous solution was lyophilized to give 8.61 g of product (76.4% yield, HPLC purity: 99%).

Synthesis of NHS ester of N-phthalimidooxyacetic acid (i): To a 50 mL of centrifuge tube was charged with 1.03 g (4.67 mmole) ofN-Phthalimidooxyacctic acid, 1.06 g (5.14 mmolc) of N,N'-Dicyclohexylcarbodiimide (DCC), 0.591 g (5.14 mmole) of N-hydroxysuccimide, and 23 mL of NMP. The mixture was vortexed for 30 seconds and then nutated at 45° C. HPLC indicates the completion of the reaction after 30 minutes (FIG. 15, left panel, N-phthalimidooxyacetic acid: $t_R$=2.0 minutes; NHS ester: $t_R$=2.3 minutes). The crude mixture was used directly for the next step without purification.

Synthesis of NHS ester of 4-(1-azi-2,2,2-trifluoromethyl) benzoic acid (o): To a 1.5 mL of ultracentrifuge tube was added 20 mg (0.0869 mmole) of 4-(1-azi-2,2,2-trifluoromethyl)benzoic acid, 21.6 mg (0.1052 mmole) of DCC, 11 mg (0.0956 mmole) of N-hydroxysuccimide, and 435 uL of dimethylformamide (DMF). The mixture was vortexed for 30 seconds, and then nutatcd at RT. HPLC indicates the completion of the reaction within an hour (FIG. 15, right panel; 4-(1-azi-2,2,2-trifluoromethyl)benzoic acid: $t_R$=3.73 minutes; NHS ester: $t_R$=3.99 minutes). The crude reaction mixture was used directly for the next step without purification.

Synthesis of j1: To a 15 mL of centrifuge tube was added 0.329 g (0.986 mmole) of N-Fmoc-2-(methylamino)-ethylamine hydrochloride, 0.488 ml (2.8 mmole) of N,N-Diisopropylethylamine (DIPEA), and 4.6 mL of 0.2 M NHS ester ((compound i) solution in NMP. The mixture was vortexed for 30 seconds and then nutated at RT. HPLC indicates the reaction was completed within an hour (FIG. 16 j1. $t_R$=9.78 minutes; Calculated exact mass: 499.17 Da; obtained: 479.3, 500.4). The product can be purified by reversed-phase HPLC column or precipitated out from the NMP by adding cold water. Around 1 mL of the crude mixture was subjected to a C18 desalting purification. The product eluted was lyophilized to dryness and used for the next reaction without further purification.

Synthesis of j2: To a 15 mL of centrifuge tube was added 0.216 g (1.027 mmole) of N-tert-butoxyearbonyl-2-(methylamino)-ethylamine hydrochloride, 0.488 ml (2.8 mmole) of DIPEA, and 4.6 mL of 0.2 M NHS ester ((compound i) solution in NMP. The mixture was vortexed for 30 seconds and then nutated at RT. HPLC indicates the reaction was completed within an hour (FIG. 16 j2. $t_R$=7.29 minutes; Calculated exact mass: 377.16 Da; obtained: 378.3, 400.5). The product can be easily purified by reverse phase HPLC column or precipitated out from the NMP by adding cold water.

Synthesis of j3: To a 15 mL of centrifuge tube was charged with 0.394 g (4.47 mmole) of 1,4-diaminobutane, 0.325 ml (1.868 mmole) of DIPEA, and 4.6 mL of 0.2 N NHS ester ((compound i) solution in NMP. The mixture was vortexed for 30 seconds and then nutatcd at RT. HPLC indicates the reaction was completed within an hour (FIG. 16 j3. $t_R$=4.14 minutes; Calculated exact mass: 291.12 Da, obtained: 292.4). The product can be easily purified by reverse phase HPLC column.

Synthesis of k1: To a 1.5 mL of centrifuge tube was added 13.1 mg (26.2 μmole) of j1 and 200 μL of 2% 1,8-diazabicyclo[5.4.0]undec-7-ene (DBU) in DMF (v/v). The mixture was vortexed for 30 seconds and then left at RT for 5 minutes. To this mixture, 153 μL of 0.17 M NHS ester (compound o) in DMF was added. The mixture was nutated at RT overnight. HPLC purification afforded product k1 (FIG. 17 $t_R$=9.12 min; Calculated exact mass: 489.13 Da, obtained: 489.8).

Synthesis of l1: To test the conditions for removing N-phthaloyl group, a small amount of purified k1 was dissolved in 2 μL of 0.124/4/1 (v/v/v) $NH_2NH_2$/Pyridine/AcOH solution. The rate of cleavage is analyzed by HPLC (5 minutes: less than 5% of product formation; 2 hr: 30% of product formation). HPLC purification afforded product l1 (FIG. 17 $t_R$=6.96 min; Calculated exact mass: 359.12 Da, obtained: 359.9).

Example 6

Synthesis of Amide Bond-Linked Multifunctional Protein Labeling Reagent on a Cleavable Solid Support FIG. 18 presents an example of a multi-functional protein labeling reagent on a cleavable solid support. This reagent has an aldehyde functional group that can react with aminooxy/hydrazine/hydrazide in the presence of reducing reagent to form a stable bond. The first tagging molecule (T1) has a quaternary amine moiety. A tertiary amine functional group is incorporated into this labeling reagent to increase the ionization efficiency of the modified peptides. The second tagging molecule (T2) has a pyrene moiety. Pyrene is very hydrophobic and, if necessary, can be used as a purification handle after cleavage from the resin. Pyrene also emits fluorescence at 384 nm and enables the detection of peptides in the picomole range.

Example 7

Isolation and/or Purification of Crosslinked Peptide Fragments Containing an Aminooxy Group The oxime bond forming reaction between aminooxy and aldehyde groups is a very efficient and selective reaction. The reaction has been successfully applied for attaching a variety of substances to proteins (Kurth et. al. *J. Med. Chem.* 1993, 36, 1255-1261; Webb et. al. *Bioconjug. Chem.* 1990, I, 96-99; Ryser et. al. *J. Nucl. Med.* 1992, 33, 1766-1773; Mikola et al. *Bioconjug. Chem.* 1992, 3, 182-186), preparing bioconjugates, such as nucleic acid-lipid (Hecker et. al. *ChemMedChem* 2008, 3, 1356-1361), peptide-drug (Ingalinella et. al. *Bioorg Med. Chem. Lett.* 2001, II, 1343-1346), peptide-oligo (Villien et al. *Nucleosides, Nucleotides& Nucleic Acids* 2004, 23, 1657-1666), and multimeric cyclic RGD peptide-ligand (Thumshim et. al. *Chem. Eur. J.* 2003, 9, 2717-2725). The oxime bond is compatible with all standard amino acid residues and is stable both in vitro and in vivo. Although there is no literature precedent for using the oxime bond as a reversible link, there are reports showing that the stability of the oxime bond varies greatly with pH (Rose K. et at Bioconjugate Chem. 1996, 7, 552-556).

FIG. 19 gives an example illustrates a solid phase-based method for the isolation of crosslinked products. Aminooxy compound reacts with aldehyde and ketone under mild acidic conditions, forming a relatively stable oxime bond. By increasing the pH, the oxime bond can be hydrolyzed. The inclusion of an excess of acetone can perform an exchange reaction with the ketone, resulting in an acetone-linked peptide. The acetone-linked peptide can be further derivatized with any aldehyde containing a fluorescent or mass tag. The conditions for oxime bond formation and the exchange reaction with acetone are very mild and physiologically, comparable. To test feasibility, a few peptides carrying an aminooxy functional group can be synthesized using the standard Fmoc-peptide synthesis protocol and Fmoc-aminooxyacetic acid. A dextrin resin or an agarose gel, modified with aldehyde- or ketone-containing compounds with various linkers, can be used as a solid support/media. The loading capacity of the support/media is determined by using an UV-active aminooxy compound. Agarose beads containing a simple aldehyde group (AminoLink resin) is also available from Pierce. The efficiency of coupling and cleaving aminooxy peptides on and from the solid support or media can be analyzed by HPLC.

INCORPORATION BY REFERENCE

The entire disclosure of each of the publications and patent documents referred to herein is incorporated by reference in its entirety for all purposes to the same extent as if each individual publication or patent document were also individually denoted.

EQUIVALENTS

The invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims rather than by the foregoing description, and all changes that come within the meaning and range of equivalency of the claims are intended to be embraced therein.

What is claimed is:

1. A crosslinking reagent having the structural Formula (L):

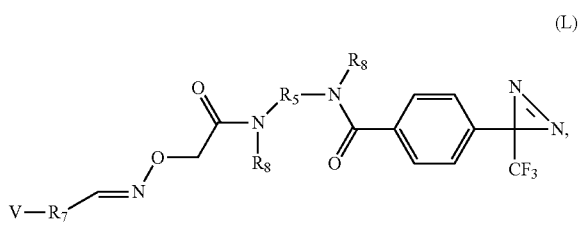

wherein V is a haloacetyl group, an alkyl halide group, a maleimide group, or an N-hydroxylsuccinimide ester group; each of $R_5$ and $R_7$ is independently selected from $-(CH_2)_n-$ and $-O(CH_2CH_2)_n-$; and wherein each n is an integer independently selected from between 1 and 16 inclusive; each $R^8$ is independently H, or an alkyl group.

2. A crosslinking reagent having the structural Formula (L'):

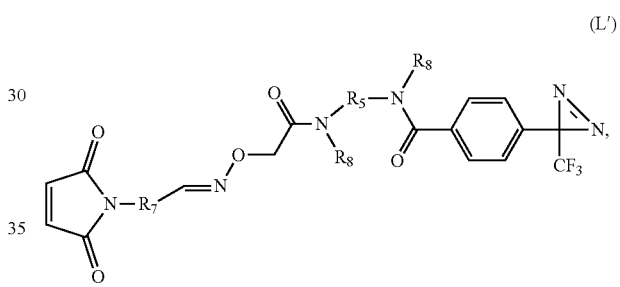

wherein each of $R_5$ and $R_7$ is independently selected from $-(CH_2)_n-$ and $-O(CH_2CH_2)_n-$; and wherein each n is an integer independently selected from between 1 and 16 inclusive; each $R^8$ is independently H, or an alkyl group.

* * * * *